(12) United States Patent
Luettgen et al.

(10) Patent No.: US 7,198,487 B2
(45) Date of Patent: Apr. 3, 2007

(54) WHITENING TIP FOR DENTAL FLOSSING DEVICE

(75) Inventors: Harold A. Luettgen, Windsor, CO (US); John Hoppes, Waterloo, IA (US); Mohan L. Sanduja, Flushing, NY (US); Carl Horowitz, Brooklyn, NY (US); Lina Zilberman, Brooklyn, NY (US); Paul Thottahil, New Hyde Park, NY (US)

(73) Assignee: Water Pik, Inc., Fort Collins, CO (US)

( * ) Notice: Subject to any disclaimer, the term of this patent is extended or adjusted under 35 U.S.C. 154(b) by 315 days.

(21) Appl. No.: 10/750,720

(22) Filed: Dec. 31, 2003

(65) Prior Publication Data

US 2004/0202981 A1 Oct. 14, 2004

Related U.S. Application Data

(60) Provisional application No. 60/445,721, filed on Feb. 7, 2003, provisional application No. 60/437,417, filed on Dec. 31, 2002.

(51) Int. Cl.
*A61C 3/03* (2006.01)
(52) U.S. Cl. .................... 433/118; 132/322
(58) Field of Classification Search ............... 433/142, 433/118, 119, 141; 132/321, 322, 323
See application file for complete search history.

(56) References Cited

U.S. PATENT DOCUMENTS

| 684,951 | A | 10/1901 | Rothkranz |
| 933,718 | A | 9/1909 | Mahoney |
| 1,033,819 | A | 7/1912 | McMann |
| 1,278,225 | A | 9/1918 | Schamberg |
| 1,313,490 | A | 8/1919 | Larson |
| 1,355,037 | A | 10/1920 | Dziuk |
| 1,424,879 | A | 8/1922 | Carlstedt |
| 1,517,320 | A | 12/1924 | Stoddart |
| 1,696,835 | A | 12/1928 | Burnett |
| 1,703,642 | A | 2/1929 | Sticht |
| 1,796,641 | A | 3/1931 | Zimmerman et al. |
| 1,800,993 | A | 4/1931 | Funk |

(Continued)

FOREIGN PATENT DOCUMENTS

| CH | 435553 | 10/1967 |
| CH | 609238 | 2/1979 |
| DE | 243224 | 4/1910 |
| DE | 1766651 C1 | 12/1981 |
| DE | 3431481 | 2/1986 |

(Continued)

OTHER PUBLICATIONS

Sonex International: Brushing with the Ultima—The World's Only Dual-Frequency Ultrasonic Toothbrush, Jul. 28, 1999, published at Sonipic.com (Continued)

*Primary Examiner*—Ralph A. Lewis
(74) *Attorney, Agent, or Firm*—Dorsey & Whitney LLP

(57) ABSTRACT

A power flosser tip incorporating a tooth-whitening coating. The coating is typically abrasive, and whitens teeth by scraping or wearing down hardened plaque or other tooth discolorations. The coating may also whiten teeth through a chemical reaction. The coating may be flavored in order to enhance user enjoyment. The coating is chemically bonded to the flosser tip, and dissolves when in contact with saliva or water at room temperature and pressure.

14 Claims, 25 Drawing Sheets

U.S. PATENT DOCUMENTS

| | | |
|---|---|---|
| 1,832,519 A | 11/1931 | Wheat et al. |
| 1,880,617 A | 10/1932 | White |
| 1,992,770 A | 2/1935 | Rathbun |
| 2,016,597 A | 10/1935 | Drake |
| 2,044,863 A | 6/1936 | Sticht |
| 2,158,738 A | 5/1939 | Baker et al. |
| 2,206,726 A | 7/1940 | Lasater |
| 2,218,072 A | 10/1940 | Runnels |
| 2,246,523 A | 6/1941 | Kulik |
| 2,278,365 A | 3/1942 | Daniels |
| 2,282,700 A | 5/1942 | Bobbroff |
| 2,405,029 A | 7/1946 | Gallanty et al. |
| 2,450,635 A | 10/1948 | Dembenski |
| 2,543,999 A | 3/1951 | Voss |
| 2,577,597 A | 12/1951 | Wright et al. |
| 2,583,750 A | 1/1952 | Runnels |
| 2,598,275 A | 5/1952 | Lakin |
| 2,709,227 A | 5/1955 | Foley et al. |
| 2,728,928 A | 1/1956 | Beeren |
| 2,734,139 A | 2/1956 | Murphy |
| 2,806,235 A | 9/1957 | Carstairs et al. |
| 2,875,458 A | 3/1959 | Tsuda |
| 2,917,758 A | 12/1959 | Held et al. |
| 2,931,371 A | 4/1960 | Petitta |
| 2,962,033 A | 11/1960 | Lew |
| 2,977,614 A | 4/1961 | Demanuele |
| 2,977,682 A | 4/1961 | Flatray |
| 3,104,405 A | 9/1963 | Perrinjaquet |
| 3,106,216 A | 10/1963 | Kirby |
| D197,048 S | 12/1963 | Troy |
| D197,208 S | 12/1963 | Cassidy et al. |
| 3,143,697 A | 8/1964 | Springer |
| 3,145,404 A | 8/1964 | Fiedler |
| D199,560 S | 11/1964 | Thompson |
| D199,893 S | 12/1964 | Bond et al. |
| 3,159,859 A | 12/1964 | Rasmussen |
| 3,181,189 A | 5/1965 | Leyden |
| 3,183,538 A | 5/1965 | Hubner |
| D202,873 S | 11/1965 | Husted |
| D204,127 S | 3/1966 | Syvertson |
| 3,270,416 A | 9/1966 | Massa |
| 3,289,681 A | 12/1966 | Chambers |
| 3,311,116 A | 3/1967 | Foster |
| 3,316,576 A | 5/1967 | Urbrush |
| 3,335,443 A | 8/1967 | Parisi et al. |
| 3,346,748 A | 10/1967 | McNair |
| 3,358,309 A | 12/1967 | Richardson |
| 3,364,576 A | 1/1968 | Kern, Jr. |
| 3,371,260 A | 2/1968 | Jackson et al. |
| 3,375,820 A | 4/1968 | Kuris et al. |
| D212,208 S | 9/1968 | Rogers |
| 3,418,552 A | 12/1968 | Holmes |
| 3,421,524 A | 1/1969 | Waters |
| 3,430,279 A | 3/1969 | Hintze |
| 3,463,994 A | 8/1969 | Spohr |
| 3,466,689 A | 9/1969 | Aurelio et al. |
| 3,472,045 A | 10/1969 | Nelsen et al. |
| 3,472,247 A | 10/1969 | Borsum et al. |
| 3,474,799 A | 10/1969 | Cappello |
| 3,509,874 A | 5/1970 | Stillman |
| 3,535,726 A | 10/1970 | Sawyer |
| 3,538,359 A | 11/1970 | Barowski |
| 3,552,022 A | 1/1971 | Axelsson |
| 3,559,292 A | 2/1971 | Weissman |
| 3,563,233 A | 2/1971 | Bodine |
| 3,588,936 A | 6/1971 | Duve |
| 3,590,814 A | 7/1971 | Bennett et al. |
| D221,823 S | 9/1971 | Cook |
| 3,608,548 A | 9/1971 | Lewis |
| 3,642,344 A | 2/1972 | Corker |
| 3,651,576 A | 3/1972 | Massa |
| 3,660,902 A | 5/1972 | Axelsson |
| 3,667,483 A | 6/1972 | McCabe |
| 3,672,378 A | 6/1972 | Silverman |
| 3,676,218 A | 7/1972 | Sawyer |
| 3,759,274 A | 9/1973 | Warner |
| 3,760,799 A | 9/1973 | Crowson |
| 3,809,977 A | 5/1974 | Balamuth et al. |
| 3,831,611 A | 8/1974 | Hendricks |
| 3,840,932 A | 10/1974 | Balamuth et al. |
| 3,847,167 A | 11/1974 | Brien |
| D234,518 S | 3/1975 | Gerlich |
| 3,882,364 A | 5/1975 | Wright et al. |
| 3,902,510 A | 9/1975 | Roth |
| 3,903,601 A | 9/1975 | Anderson et al. |
| 3,967,617 A | 7/1976 | Krolik |
| 3,978,852 A | 9/1976 | Annoni |
| 3,980,906 A | 9/1976 | Kuris et al. |
| 4,004,344 A | 1/1977 | Gold et al. |
| 4,005,722 A | 2/1977 | Bragg |
| 4,008,728 A | 2/1977 | Sanchez |
| 4,014,354 A | 3/1977 | Garrett |
| 4,019,522 A | 4/1977 | Elbreder |
| 4,048,723 A | 9/1977 | Thorup |
| 4,064,883 A | 12/1977 | Oldham |
| 4,133,339 A | 1/1979 | Naslund |
| 4,177,434 A | 12/1979 | Ida |
| D254,162 S | 2/1980 | Barker |
| 4,192,035 A | 3/1980 | Kuris |
| 4,203,431 A | 5/1980 | Abura et al. |
| 4,205,664 A | 6/1980 | Baccialon |
| 4,219,619 A | 8/1980 | Zarow |
| 4,235,253 A | 11/1980 | Moore |
| 4,245,658 A | 1/1981 | Lecouturier |
| RE30,536 E | 3/1981 | Perdreaux, Jr. |
| 4,255,693 A | 3/1981 | Keidl |
| 4,265,257 A | 5/1981 | Salyer |
| 4,271,382 A | 6/1981 | Maeda et al. |
| 4,271,384 A | 6/1981 | Beling et al. |
| 4,271,854 A | 6/1981 | Bengtsson |
| 4,275,363 A | 6/1981 | Mishiro et al. |
| 4,289,486 A | 9/1981 | Sargeant |
| 4,303,064 A | 12/1981 | Buffa |
| 4,307,740 A | 12/1981 | Florindez et al. |
| 4,319,377 A | 3/1982 | Tarrson et al. |
| 4,319,595 A | 3/1982 | Ulrich |
| 4,326,547 A | 4/1982 | Verplank |
| 4,326,548 A | 4/1982 | Wagner |
| 4,326,549 A | 4/1982 | Hinding |
| 4,331,422 A | 5/1982 | Heyman |
| 4,333,197 A | 6/1982 | Kuris |
| 4,336,622 A | 6/1982 | Teague, Jr. et al. |
| D265,515 S | 7/1982 | Levine |
| 4,338,957 A | 7/1982 | Meibauer |
| 4,346,492 A | 8/1982 | Solow |
| 4,347,839 A | 9/1982 | Youngclaus, Jr. |
| 4,353,141 A | 10/1982 | Teague, Jr. et al. |
| 4,356,585 A | 11/1982 | Protell et al. |
| 4,381,478 A | 4/1983 | Saijo et al. |
| 4,395,665 A | 7/1983 | Buchas |
| 4,397,327 A | 8/1983 | Hadary |
| D272,565 S | 2/1984 | Levine |
| D272,680 S | 2/1984 | Stocchi |
| 4,429,997 A | 2/1984 | Matthews |
| 4,432,729 A | 2/1984 | Fattaleh |
| 4,434,806 A | 3/1984 | Givens |
| 4,442,830 A | 4/1984 | Markau |
| 4,450,599 A | 5/1984 | Scheller et al. |
| 4,455,704 A | 6/1984 | Williams |
| 4,458,702 A | 7/1984 | Grollimund |
| 4,488,327 A | 12/1984 | Snider |
| 4,490,114 A | 12/1984 | Kleesattel |
| 4,505,678 A | 3/1985 | Andersson |
| 4,522,355 A | 6/1985 | Moran |

| | | | | | | |
|---|---|---|---|---|---|---|
| 4,522,595 | A | 6/1985 | Selvidge | 5,120,225 | A | 6/1992 | Amit |
| 4,543,679 | A | 10/1985 | Rosofsky et al. | 5,123,841 | A | 6/1992 | Millner |
| 4,562,413 | A | 12/1985 | Mishiro et al. | 5,125,837 | A | 6/1992 | Warrin et al. |
| 4,564,794 | A | 1/1986 | Kilen et al. | 5,133,661 | A | 7/1992 | Euvrard |
| 4,576,190 | A | 3/1986 | Youssef | 5,138,733 | A | 8/1992 | Bock |
| 4,577,649 | A | 3/1986 | Shimenkov | 5,145,369 | A | 9/1992 | Lustig et al. |
| 4,578,033 | A | 3/1986 | Mossle et al. | 5,146,643 | A | 9/1992 | Bojar et al. |
| D283,374 | S | 4/1986 | Cheuk-Yiu | 5,150,492 | A | 9/1992 | Suroff |
| 4,585,415 | A | 4/1986 | Hommann | 5,151,030 | A | 9/1992 | Comeaux |
| 4,586,521 | A | 5/1986 | Urso | 5,152,394 | A | 10/1992 | Hughes |
| 4,603,448 | A | 8/1986 | Middleton et al. | 5,163,375 | A | 11/1992 | Withers et al. |
| 4,605,025 | A | 8/1986 | McSpadden | 5,165,131 | A | 11/1992 | Staar |
| 4,608,019 | A | 8/1986 | Kumabe et al. | 5,167,193 | A | 12/1992 | Withers et al. |
| 4,610,043 | A | 9/1986 | Vezjak | 5,169,313 | A | 12/1992 | Kline |
| 4,617,718 | A | 10/1986 | Andersson | 5,170,809 | A | 12/1992 | Imai et al. |
| 4,634,376 | A | 1/1987 | Mossle et al. | 5,174,314 | A | 12/1992 | Charatan |
| 4,644,937 | A | 2/1987 | Hommann | 5,176,157 | A | 1/1993 | Mazza |
| 4,655,198 | A | 4/1987 | Hommann | 5,177,826 | A | 1/1993 | Vrignaud et al. |
| 4,698,869 | A | 10/1987 | Mierau et al. | 5,180,363 | A | 1/1993 | Idemoto et al. |
| 4,706,695 | A | 11/1987 | Urso | 5,183,063 | A | 2/1993 | Ringle et al. |
| D294,885 | S | 3/1988 | Mollenhoff | 5,183,156 | A | 2/1993 | Bruno |
| 4,766,630 | A | 8/1988 | Hegemann | 5,184,368 | A | 2/1993 | Holland |
| 4,787,847 | A | 11/1988 | Martin et al. | 5,184,632 | A | 2/1993 | Gross et al. |
| 4,791,940 | A | 12/1988 | Hirschfeld et al. | 5,186,191 | A | 2/1993 | Loubier |
| 4,811,445 | A | 3/1989 | Lagieski et al. | 5,188,133 | A | 2/1993 | Romanus |
| 4,820,153 | A | 4/1989 | Romhild et al. | 5,189,751 | A | 3/1993 | Giuliani et al. |
| 4,820,154 | A | 4/1989 | Romhild et al. | 5,193,678 | A | 3/1993 | Janocik et al. |
| 4,827,550 | A | 5/1989 | Graham et al. | 5,198,732 | A | 3/1993 | Morimoto |
| 4,832,063 | A | 5/1989 | Smole | 5,201,092 | A | 4/1993 | Colson |
| 4,844,104 | A | 7/1989 | Martin | 5,207,773 | A | 5/1993 | Henderson |
| 4,845,795 | A | 7/1989 | Crawford et al. | 5,213,434 | A | 5/1993 | Hahn |
| 4,856,133 | A | 8/1989 | Sanchez | 5,214,819 | A | 6/1993 | Kirchner |
| D303,876 | S | 10/1989 | Clemens et al. | 5,217,031 | A | 6/1993 | Santoro |
| 4,871,396 | A | 10/1989 | Tsujita et al. | 5,224,500 | A | 7/1993 | Stella |
| 4,873,496 | A | 10/1989 | Ohgihara et al. | 5,226,206 | A | 7/1993 | Davidovitz et al. |
| 4,875,265 | A | 10/1989 | Yoshida | 5,236,358 | A | 8/1993 | Sieffert |
| 4,877,934 | A | 10/1989 | Spinello | 5,245,117 | A | 9/1993 | Withers et al. |
| 4,879,781 | A | 11/1989 | Desimone | 5,246,022 | A | 9/1993 | Israel et al. |
| 4,880,382 | A | 11/1989 | Moret et al. | 5,247,716 | A | 9/1993 | Bock |
| 4,887,052 | A | 12/1989 | Murakami et al. | 5,253,382 | A | 10/1993 | Beny |
| 4,892,191 | A | 1/1990 | Nakamura | 5,261,430 | A | 11/1993 | Mochel |
| 4,908,902 | A | 3/1990 | McNab et al. | 5,263,218 | A | 11/1993 | Giuliani et al. |
| 4,913,133 | A | 4/1990 | Tichy | D341,943 | S | 12/1993 | Si-Hoe |
| 4,913,176 | A | 4/1990 | DeNiro | 5,267,579 | A | 12/1993 | Bushberger |
| 4,922,936 | A | 5/1990 | Buzzi et al. | 5,279,314 | A | 1/1994 | Poulos et al. |
| 4,974,278 | A | 12/1990 | Hommann | 5,289,604 | A | 3/1994 | Kressner |
| 4,989,287 | A | 2/1991 | Scherer | 5,293,886 | A | 3/1994 | Czapor |
| 4,991,249 | A | 2/1991 | Suroff | 5,294,896 | A | 3/1994 | Kjellander et al. |
| 4,995,403 | A | 2/1991 | Beckman et al. | 5,299,723 | A | 4/1994 | Hempel |
| 5,000,684 | A | 3/1991 | Odrich | 5,305,492 | A | 4/1994 | Giuliani et al. |
| 5,002,487 | A | 3/1991 | Tichy | 5,309,590 | A | 5/1994 | Giuliani et al. |
| 5,007,127 | A | 4/1991 | Paolo | 5,309,591 | A | 5/1994 | Heägele et al. |
| 5,016,660 | A | 5/1991 | Boggs | 5,311,632 | A | 5/1994 | Center |
| 5,020,179 | A | 6/1991 | Scherer | 5,311,633 | A | 5/1994 | Herzog et al. |
| 5,033,150 | A | 7/1991 | Gross et al. | 5,323,796 | A | 6/1994 | Urso |
| D319,363 | S | 8/1991 | Uemura et al. | 5,337,435 | A | 8/1994 | Krasner et al. |
| 5,050,625 | A | 9/1991 | Siekmann | 5,339,482 | A | 8/1994 | Desimone et al. |
| D321,285 | S | 11/1991 | Hirabayashi | 5,341,534 | A | 8/1994 | Serbinski et al. |
| 5,062,797 | A | 11/1991 | Gonser | 5,353,460 | A | 10/1994 | Bauman |
| 5,067,223 | A | 11/1991 | Bruno | 5,354,246 | A | 10/1994 | Gotman |
| D321,986 | S | 12/1991 | Snyder et al. | 5,355,638 | A | 10/1994 | Hoffman |
| 5,068,939 | A | 12/1991 | Holland | 5,358,328 | A | 10/1994 | Inoue et al. |
| 5,069,233 | A | 12/1991 | Ritter | 5,359,747 | A | 11/1994 | Amakasu |
| 5,069,621 | A | 12/1991 | Paradis | D353,490 | S | 12/1994 | Hartwein |
| 5,071,348 | A | 12/1991 | Woog | 5,369,831 | A | 12/1994 | Bock |
| 5,072,477 | A | 12/1991 | Pai | D354,168 | S | 1/1995 | Hartwein |
| 5,072,482 | A | 12/1991 | Bojar et al. | 5,378,153 | A | 1/1995 | Giuliani et al. |
| 5,077,855 | A | 1/1992 | Ambasz | 5,383,242 | A | 1/1995 | Bigler et al. |
| 5,085,236 | A | 2/1992 | Odneal et al. | 5,393,229 | A | 2/1995 | Ram |
| 5,088,145 | A | 2/1992 | Whitefield | 5,400,811 | A | 3/1995 | Meibauer |
| 5,094,256 | A | 3/1992 | Barth | 5,404,608 | A | 4/1995 | Hommann |
| 5,095,470 | A | 3/1992 | Oka et al. | 5,406,664 | A | 4/1995 | Hukuba |
| 5,100,321 | A | 3/1992 | Coss et al. | 5,406,965 | A | 4/1995 | Levine |

| | | | | | | |
|---|---|---|---|---|---|---|
| D358,486 S | 5/1995 | Loew | | D400,713 S | 11/1998 | Solanki |
| D358,713 S | 5/1995 | Perry | | 5,836,030 A | 11/1998 | Hazeu et al. |
| D358,801 S | 5/1995 | Vos | | 5,842,244 A | 12/1998 | Hilfinger et al. |
| 5,411,041 A | 5/1995 | Ritter | | 5,850,655 A | 12/1998 | Göcking et al. |
| 5,412,827 A | 5/1995 | Muller et al. | | 5,851,514 A * | 12/1998 | Hassan et al. ............... 424/53 |
| 5,416,942 A | 5/1995 | Baldacci et al. | | D403,511 S | 1/1999 | Serbinski |
| 5,419,346 A | 5/1995 | Tipp | | 5,855,216 A | 1/1999 | Robinson |
| 5,419,703 A | 5/1995 | Warrin et al. | | 5,862,558 A | 1/1999 | Hilfinger et al. |
| 5,421,726 A | 6/1995 | Okada | | 5,864,915 A | 2/1999 | Ra |
| 5,438,726 A | 8/1995 | Leite | | 5,867,856 A | 2/1999 | Herzog |
| D363,605 S | 10/1995 | Kou et al. | | 5,875,797 A * | 3/1999 | Chiang et al. ............. 132/321 |
| 5,459,898 A | 10/1995 | Bacolot | | 5,893,175 A | 4/1999 | Cooper |
| 5,467,494 A | 11/1995 | Muller et al. | | 5,896,615 A | 4/1999 | Zaksenberg |
| 5,467,495 A | 11/1995 | Boland et al. | | 5,899,693 A | 5/1999 | Himeno et al. |
| 5,482,466 A | 1/1996 | Haynes | | 5,900,230 A * | 5/1999 | Cutler ........................ 424/49 |
| 5,484,281 A | 1/1996 | Renow et al. | | D410,787 S | 6/1999 | Barre et al. |
| 5,496,256 A | 3/1996 | Bock et al. | | 5,908,038 A | 6/1999 | Bennett |
| 5,499,420 A | 3/1996 | Boland | | 5,921,254 A | 7/1999 | Carlucci et al. |
| 5,504,958 A | 4/1996 | Herzog | | 5,927,300 A | 7/1999 | Boland et al. |
| 5,511,270 A | 4/1996 | Eliachar et al. | | 5,930,858 A | 8/1999 | Jung |
| 5,511,275 A | 4/1996 | Volpenhein et al. | | 5,931,170 A | 8/1999 | Wu |
| D370,125 S | 5/1996 | Craft et al. | | 5,943,723 A | 8/1999 | Hilfinger et al. |
| 5,518,012 A * | 5/1996 | Dolan et al. ................ 132/321 | | 5,944,033 A | 8/1999 | Robinson |
| D370,347 S | 6/1996 | Heinzelman et al. | | D413,694 S | 9/1999 | Bennett |
| 5,529,494 A | 6/1996 | Vlacancich | | D414,937 S | 10/1999 | Cornu et al. |
| D371,242 S | 7/1996 | Shimatsu et al. | | D414,939 S | 10/1999 | Pedro, Jr. et al. |
| 5,530,981 A | 7/1996 | Chen | | 5,974,613 A | 11/1999 | Herzog |
| 5,544,382 A | 8/1996 | Giuliani et al. | | 5,974,615 A | 11/1999 | Schwarz-Hartmann et al. |
| 5,545,968 A | 8/1996 | Hilfinger et al. | | 5,980,541 A | 11/1999 | Tenzer |
| 5,546,624 A | 8/1996 | Bock | | 5,987,681 A | 11/1999 | Hahn et al. |
| 5,546,626 A | 8/1996 | Chung | | 5,991,957 A | 11/1999 | Watanabe |
| 5,561,881 A | 10/1996 | Klinger et al. | | D417,960 S | 12/1999 | Moskovich et al. |
| D375,841 S | 11/1996 | Serbinski | | 6,000,083 A | 12/1999 | Blaustein et al. |
| 5,573,020 A | 11/1996 | Robinson | | 6,009,589 A | 1/2000 | Driesen et al. |
| 5,577,285 A | 11/1996 | Drossler | | 6,021,538 A | 2/2000 | Kressner et al. |
| D376,695 S | 12/1996 | Tveras | | 6,032,313 A | 3/2000 | Tsang |
| 5,579,786 A | 12/1996 | Wolk et al. | | 6,035,476 A | 3/2000 | Underwood et al. |
| 5,584,690 A | 12/1996 | Maassarani | | 6,047,711 A | 4/2000 | Wagner |
| 5,588,452 A | 12/1996 | Peck | | 6,050,818 A | 4/2000 | Boland et al. |
| 5,606,984 A | 3/1997 | Gao | | D423,784 S | 5/2000 | Joulin |
| 5,613,258 A | 3/1997 | Hilfinger et al. | | 6,065,176 A | 5/2000 | Watanabe et al. |
| 5,613,259 A | 3/1997 | Craft et al. | | 6,081,957 A | 7/2000 | Webb |
| 5,617,601 A | 4/1997 | McDougall | | 6,095,811 A | 8/2000 | Stearns |
| 5,618,275 A | 4/1997 | Bock | | 6,102,700 A | 8/2000 | Haczek et al. |
| 5,619,766 A | 4/1997 | Zhadanov et al. | | 6,165,131 A | 12/2000 | Cuse et al. |
| 5,623,746 A | 4/1997 | Ichiro | | D437,090 S | 1/2001 | Lang et al. |
| 5,625,916 A | 5/1997 | McDougall | | D437,091 S | 1/2001 | Lang et al. |
| D381,468 S | 7/1997 | Dolan et al. | | D437,663 S | 2/2001 | Lang et al. |
| 5,651,157 A | 7/1997 | Hahn | | D437,976 S | 2/2001 | Narayanan et al. |
| D382,407 S | 8/1997 | Craft et al. | | D437,977 S | 2/2001 | Lang et al. |
| 5,652,990 A | 8/1997 | Driesen et al. | | D438,306 S | 2/2001 | Narayanan |
| 5,653,591 A | 8/1997 | Loge | | 6,183,254 B1 | 2/2001 | Cohen |
| 5,678,274 A | 10/1997 | Liu | | 6,220,857 B1 | 4/2001 | Abels |
| 5,678,578 A | 10/1997 | Kossak et al. | | 6,233,773 B1 | 5/2001 | Karge et al. |
| 5,697,117 A | 12/1997 | Craft | | 6,253,404 B1 | 7/2001 | Boland et al. |
| 5,700,146 A | 12/1997 | Kucar | | 6,267,593 B1 | 7/2001 | Haczek et al. |
| RE35,712 E | 1/1998 | Murayama | | 6,299,444 B1 | 10/2001 | Cohen |
| 5,704,087 A | 1/1998 | Strub | | 6,349,442 B1 | 2/2002 | Cohen et al. |
| 5,709,233 A | 1/1998 | Boland et al. | | 6,360,398 B1 | 3/2002 | Wiegner et al. |
| 5,718,667 A | 2/1998 | Sugimoto et al. | | 6,375,459 B1 | 4/2002 | Kamen et al. |
| 5,732,433 A | 3/1998 | Göcking et al. | | RE36,699 E | 5/2002 | Murayama |
| 5,738,575 A | 4/1998 | Bock | | 6,422,867 B2 | 7/2002 | Lang et al. |
| 5,742,972 A | 4/1998 | Bredall et al. | | D463,627 S | 9/2002 | Lang et al. |
| 5,749,380 A | 5/1998 | Zebuhr | | 6,447,293 B1 | 9/2002 | Sokol et al. |
| 5,762,078 A | 6/1998 | Zebuhr | | 6,526,994 B1 | 3/2003 | Santoro |
| 5,775,346 A | 7/1998 | Szyszkowski | | 6,609,527 B2 * | 8/2003 | Brown ....................... 132/321 |
| 5,784,742 A | 7/1998 | Giuliani et al. | | 6,609,910 B2 * | 8/2003 | Narayanan ................. 433/118 |
| 5,784,743 A | 7/1998 | Shek | | 6,659,674 B2 | 12/2003 | Carlucci et al. |
| 5,787,908 A | 8/1998 | Robinson | | 6,785,929 B2 | 9/2004 | Fritsch et al. |
| 5,794,295 A | 8/1998 | Shen | | 2001/0039955 A1 | 11/2001 | Winters et al. |
| 5,815,872 A | 10/1998 | Meginnis, III et al. | | 2002/0059685 A1 | 5/2002 | Paffrath |
| 5,816,271 A | 10/1998 | Urso | | 2002/0078974 A1 | 6/2002 | Kossak et al. |
| 5,827,064 A | 10/1998 | Bock | | 2002/0106607 A1 | 8/2002 | Horowitz |

| | | | |
|---|---|---|---|
| 2002/0112737 A1* | 8/2002 | Marcon et al. ............. 132/321 |
| 2002/0121283 A1 | 9/2002 | Piccolo et al. |
| 2002/0137728 A1* | 9/2002 | Montgomery ................ 514/99 |
| 2002/0170570 A1 | 11/2002 | Bergman |
| 2002/0178519 A1 | 12/2002 | Zarlengo |
| 2002/0185149 A1 | 12/2002 | Ali |
| 2003/0005544 A1 | 1/2003 | Felix |
| 2003/0029472 A1 | 2/2003 | Adler |
| 2003/0064348 A1 | 4/2003 | Sokol et al. |
| 2003/0098037 A1 | 5/2003 | Dougan et al. |
| 2003/0106565 A1 | 6/2003 | Andrews |
| 2003/0111091 A1 | 6/2003 | Hotta et al. |
| 2003/0140937 A1 | 7/2003 | Cook |
| 2003/0140939 A1 | 7/2003 | Nudo, Sr. |
| 2003/0150474 A1 | 8/2003 | Doyscher |
| 2003/0162146 A1 | 8/2003 | Shortt et al. |
| 2003/0196677 A1 | 10/2003 | Wiseman |
| 2004/0063603 A1* | 4/2004 | Dave et al. ................. 510/438 |
| 2005/0004498 A1 | 1/2005 | Klupt |
| 2005/0189000 A1 | 9/2005 | Cacka et al. |
| 2005/0255427 A1 | 11/2005 | Shortt et al. |
| 2005/0266376 A1 | 12/2005 | Sokol et al. |

FOREIGN PATENT DOCUMENTS

| | | |
|---|---|---|
| DE | 3512190 A1 | 10/1986 |
| DE | 8626725 | 5/1987 |
| DE | 3736308 A1 | 7/1989 |
| DE | 4142404 C2 | 7/1991 |
| DE | 4003305 A1 | 8/1991 |
| DE | 4223195 A1 | 1/1994 |
| DE | 4223196 A1 | 1/1994 |
| DE | 4226658 | 2/1994 |
| DE | 4226659 A1 | 2/1994 |
| DE | 4241576 | 6/1994 |
| DE | 4309078 A1 | 9/1994 |
| DE | 29715234 U1 | 12/1997 |
| DE | 19961447 | 7/2001 |
| EP | 0210094 | 6/1986 |
| EP | 0354352 | 2/1990 |
| EP | 0661025 B1 | 7/1995 |
| FR | 429447 | 9/1911 |
| FR | 1171337 | 1/1959 |
| GB | 477799 | 1/1938 |
| GB | 500517 | 2/1939 |
| GB | 899618 | 6/1962 |
| GB | 1583558 | 8/1977 |
| GB | 2175494 | 12/1986 |
| JP | 53-33753 | 3/1978 |
| JP | 3-222905 A | 10/1991 |
| SE | 324221 | 5/1970 |
| WO | WO 91/13570 | 9/1991 |
| WO | WO 91/19437 | 12/1991 |
| WO | WO 92/10146 | 6/1992 |
| WO | WO 92/16160 | 10/1992 |
| WO | WO 93/10721 | 6/1993 |
| WO | WO 93/15628 | 8/1993 |
| WO | WO 94/04093 | 3/1994 |
| WO | WO 94/26144 | 11/1994 |
| WO | WO 95/02375 | 1/1995 |
| WO | WO 95/33419 | 12/1995 |
| WO | WO 98/47443 | 10/1998 |
| WO | WO 01/28452 | 4/2001 |
| WO | WO 01/45582 | 6/2001 |
| WO | WO 02/071970 | 9/2002 |
| WO | WO 02/071971 | 9/2002 |

OTHER PUBLICATIONS

Teledyne Water Pik "Plaque Control 3000" plaque removal instrument (Jul. 1991).

American Dentronics Inc. "Soniplak" sonic plaque removal system (May 1993).

Design of a Toothbrush, p. 361, Danish Official Design Gazette, published May 16, 1997.

Teledyne Water Pik "Sensonic" Toothbrush, sales brochure (at least as early as Sep. 1994).

* cited by examiner

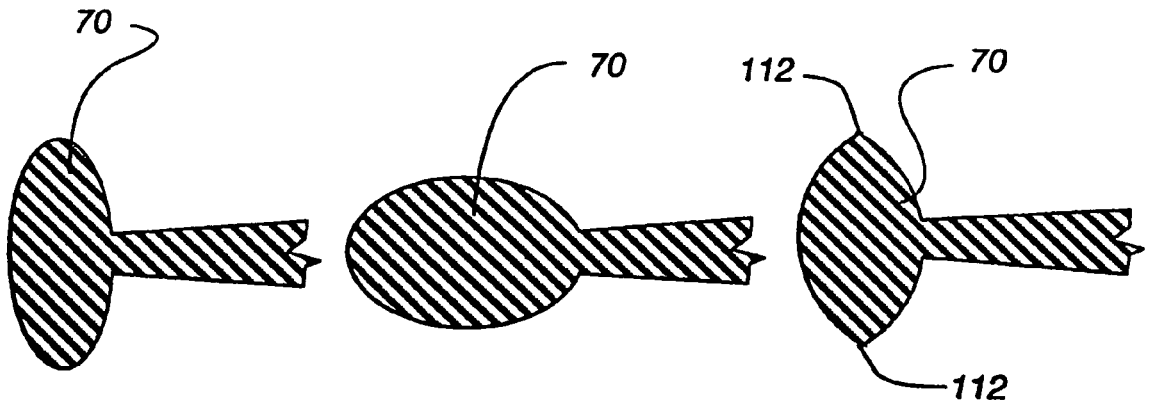
Fig. 19F    Fig. 19G    Fig. 19H
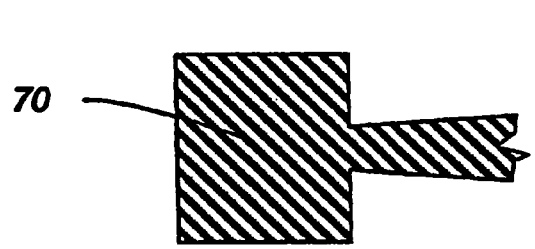 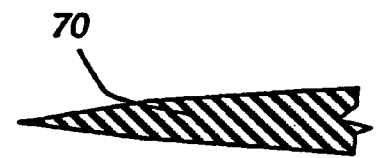
Fig. 19I    Fig. 19J
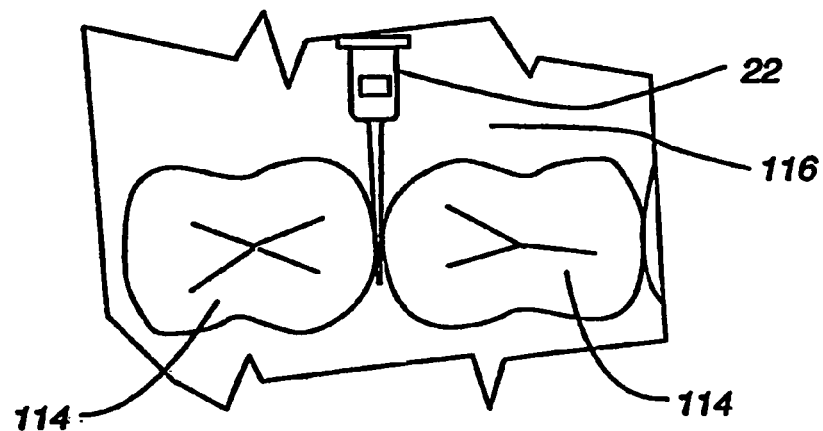
Fig. 20

WHITENING TIP FOR DENTAL FLOSSING DEVICE

CROSS-REFERENCE TO RELATED APPLICATIONS

This application claims priority to U.S. Provisional Application Ser. No. 60/445,721, filed Feb. 7, 2003 and entitled "Whitening Tip for Dental Flossing Device," and U.S. Provisional Application Ser. No. 60/437,417, filed Dec. 31, 2002 and entitled "Whitening Tip for Dental Flossing Device," both of which are incorporated by reference as if fully set forth herein in their entireties.

BACKGROUND OF THE INVENTION

1. Technical Field

This invention relates generally to a tooth-whitening tip for use with a flossing device, and more specifically to a power flosser tip having an abrasive tooth-whitening coating.

2. Background Art

Power dental flossing devices are motorized devices used to clean or floss the area between a user's teeth and between the teeth and surrounding gums. A power dental flossing device is provided with a removable tip for placement in the interdental or interproximal space between adjacent teeth and in the pockets between the teeth and gums. When the power dental flossing device is activated, the tip, if properly oriented, contacts and rubs against portions of the sides of adjacent teeth and between the gum and adjacent teeth, and helps to dislodge particles and remove plaque forming in those locations.

Conventional tips have a circular or square cross-section, and typically provide only one contact point along the side of a tooth being cleaned. One problem, which can occur with a power dental flossing device, is that ineffective cleaning may result if the tip is mis-oriented when inserted into the interproximal space between teeth. In particular, when the tip is mis-oriented, the area of the surface to be cleaned, contacted and accessed by the tip, is reduced thus reducing the efficiency of the cleaning. Further, a mis-oriented tip is more likely to break during use, or may become stuck between teeth.

In addition, a growing market has developed for tooth-whitening products. More and more people are seeking simple, cost-effective methods for whitening their teeth. Presently, most whitening solutions are either chemical or abrasive. Chemical-based whiteners are effective, but costly and time-consuming. Current abrasive whiteners may be minimally effective, and may require multiple applications to produce any visible effect. Further, both types of whiteners may require users to perform additional steps beyond brushing and flossing, such as wearing dental trays or applying strips to the teeth. These processes take up inordinate amounts of a user's time.

What is needed is a tip for a power dental flossing device which meets the aforementioned needs.

SUMMARY OF THE INVENTION

In light of the above, and according to a broad aspect of the invention, disclosed herein is a flossing tip for a power dental flossing device. The flossing tip is elongated and includes a base portion, a central portion, and an end portion. The base portion supports the tip when the tip is connected to the dental flossing device. The central portion has a substantially rectangular cross-section, and couples the base portion to the end portion. The end portion is inserted between a pair of adjacent teeth of a user, and helps guide the tip between the adjacent teeth. When in use, the substantially rectangular cross-section of the tip provides multiple points of contact against a tooth for cleaning, and also helps maintain the tip in proper orientation with respect to the teeth, thus providing more effective cleaning.

According to another broad aspect of the invention, the central portion has a top and a bottom surface, and a pair of sides, wherein the height of the sides is larger than the width of the top and bottom surfaces. The sides contact and engage the sides of the teeth, and in this manner, the tip is less likely to be rotated and mis-oriented once the tip is inserted between the teeth. In one example of the present invention, the sides of the central portion of the tip are curved, preferably inwardly.

The cross-sectional area of the tip along the central portion decreases along the length of the tip from the base portion to the end portion. The central portion has a top surface having a first width at the base portion, and a second smaller width proximate the end portion. Likewise, the height of the sides of the central portion decreases from the base portion to the end portion. In order to reduce the possibility of damage to the gums such as by poking, the edges of at least the central portion are rounded and the end portion of the tip is curved.

In another embodiment of the present invention, the tip has at least one strip of reinforcing material embedded with the central portion, for improved durability of the tip while maintaining the general flexibility of the tip.

In a further embodiment of the present invention, the tip has a disk-shaped end portion. The disc-shaped end portion helps guide the tip between the teeth in the proper orientation and further provide additional cleaning edges. It also acts as a relatively blunt leading edge to reduce aggravation of sensitive gums.

According to another broad aspect of the invention, a method of flossing teeth with a dental flossing device is disclosed. The method includes the step of providing a tip with a substantially rectangular cross-section adapted to be inserted between a pair of teeth of a user, the tip adapted to be attached to the dental flossing device. The user then inserts the tip between the pair of teeth, and activates the power dental flossing device, thereby moving the tip at least vertically upwardly and downwardly along at least a portion of one side of the pair of teeth, or between a tooth and the surrounding gum, for cleaning.

The flosser tip may also incorporate a coating, such as a whitening compound. The whitening compound aids in removing tooth discolorations through an abrasive or chemical action. The compound typically incorporates fine silica particles in order to scrub discolorations or yellowed tooth surfaces. Because the tip may be inserted into the gap between teeth, it is particularly useful for cleaning hard-to-reach interproximal areas. The compound reacts with saliva or water, causing the compound to foam and dissolve. The foaming action enhances the compound's abrasive cleaning properties and taste, while the dissolution inherently limits the usable life of the tip. Further, the coating may include an appetizing flavoring designed to enhance the user's brushing enjoyment. The tip may, for example, have a base portion for supporting the tip when coupled to the dental flossing device, a central portion having a substantially rectangular cross-section, and having a first end and a second end, said first end coupled to said base portion, wherein said central portion has a height and a width, an end portion coupled to said second end of said central portion, for insertion between a pair of adjacent teeth of a user, wherein said end portion has a height and a width, and a whitening compound substantially enclosing said end portion.

The aforementioned whitening compound may be bonded to the flosser tip, and may include a variety of chemicals or compounds making up the whitening compound. Among others, the whitening compound may include a drying retardant agent, an acrylic prepolymer, a wetting agent, and an abrasive agent.

The whitening compound is generally added to a flosser tip by a manufacturing apparatus. The manufacturing apparatus includes a feed hopper sized to contain at least one flosser tip, a spiral track operatively connected to the feed hopper, the spiral track operative to align the at least one flosser tip, a conveyor operatively connected to the spiral track, the conveyor transporting the at least one flosser tip, a vat operatively connected to the conveyor, the vat containing a whitening compound, the vat operative to receive at least a portion of the at least one flosser tip into the whitening compound to form at least one whitening flosser tip, and a drying tunnel operatively connected to the vat, the drying tunnel operative to dry the whitening compound on the at least one whitening flosser tip.

The foregoing and other features, utilities and advantages of the invention will be apparent from the following more particular description of a preferred embodiment of the invention as illustrated in the accompanying drawings and claims.

BRIEF DESCRIPTION OF THE DRAWINGS

FIG. 20 is the power dental flossing device tip in FIGS. 13–15, in accordance with one embodiment of the present invention, inserted between a pair of adjacent teeth during use.

DETAILED DESCRIPTION OF A PREFERRED EMBODIMENT

Figure 1:
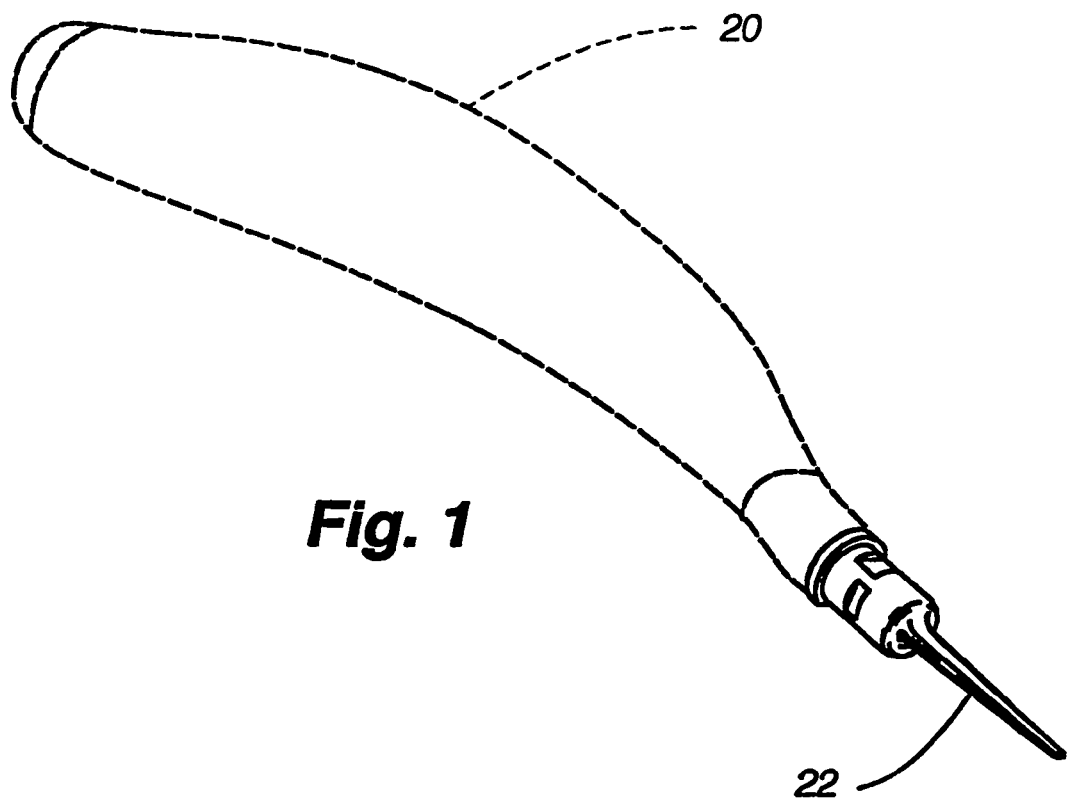
FIG. 1 illustrates an isometric view of a power dental flossing device having a tip, in accordance with one embodiment of the present invention, attached thereto.

Referring to FIG. 1, a power dental flossing device 20 incorporating a flossing tip 22 of the present invention is disclosed. The flossing tip is generally elongated and has a generally rectangular cross-section of decreasing size along the length of the tip, terminating at an end, which is inserted within the space between a pair of teeth. The tip 22 is resilient, flexible, compressible, and generally capable of withstanding forces imposed during the cleaning action. In one embodiment of the present invention, the tip 22 is made from materials such as Isoplast, Polybutylene Teriphthalate (PBT), acetal, ZYTEL™ (preferably type 101L) by DUPONT, nylon such as type 6/6, glass-filled material, or the like.

Figure 9:
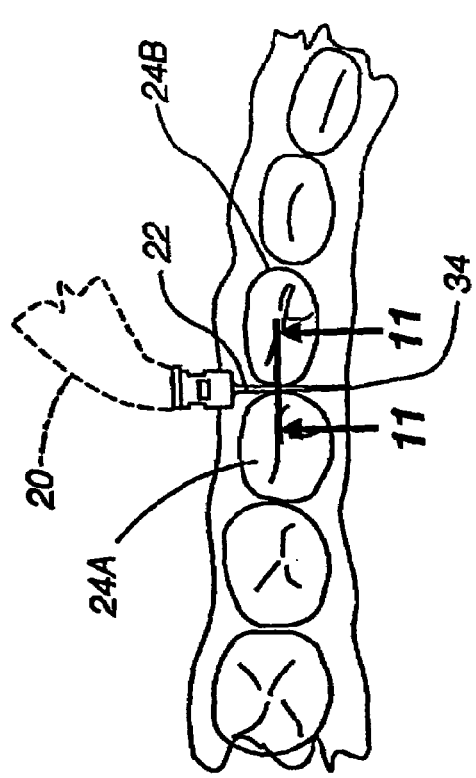
FIG. 9 illustrates a power dental flossing device with a tip in accordance with one embodiment of the present invention, inserted between a pair of adjacent teeth during use.
Figure 11:
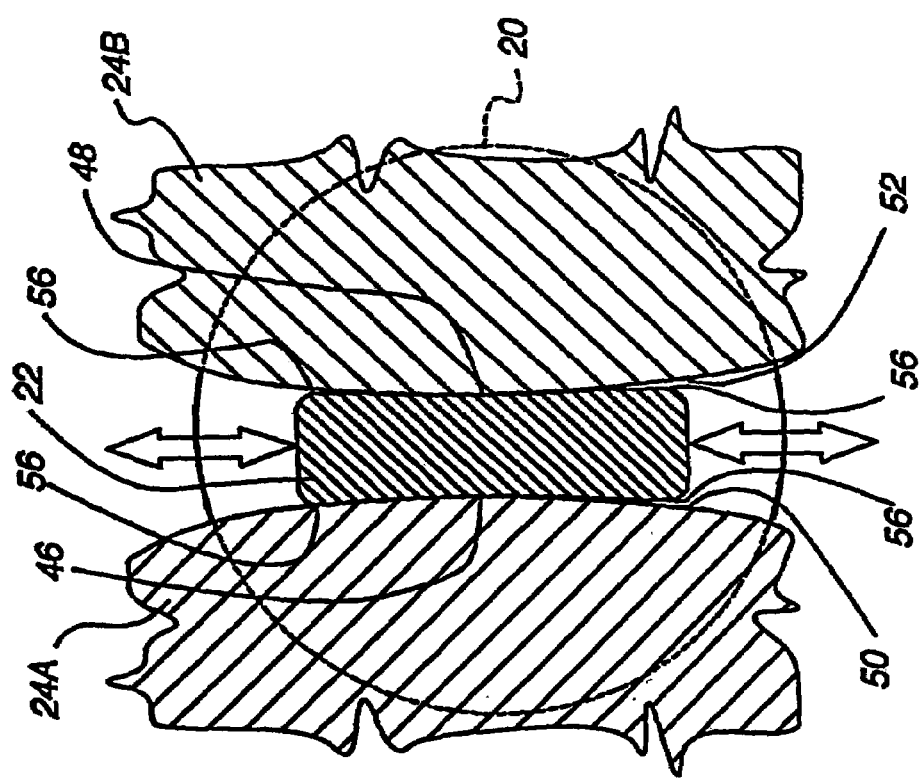
FIG. 11 is an exploded sectional view taken along section lines 11—11 of FIG. 9, and illustrates a tip in accordance with one embodiment of the present invention, inserted between a pair of adjacent teeth as the tip moves vertically upwardly and downwardly during use.

The tip 22 is adapted for use with a power dental flossing device 20, as shown in FIGS. 1 and 9, where the tip 22 is inserted by a user between adjacent teeth 24A, 24B for flossing. In one example of the present invention, the power dental flossing device 20 is a motorized device which is adapted to move the tip 22 in a linear direction, such as in a vertical direction upwardly and downwardly, during use as shown in FIG. 11. As will be described below, due to the unique shape of the tip 22 of the present invention, the tip provides multiple points of contact with the teeth being cleaned and maintains the proper orientation of the tip between teeth, which generally improves the effectiveness of the cleaning action of the power dental flossing device.

Figure 2:
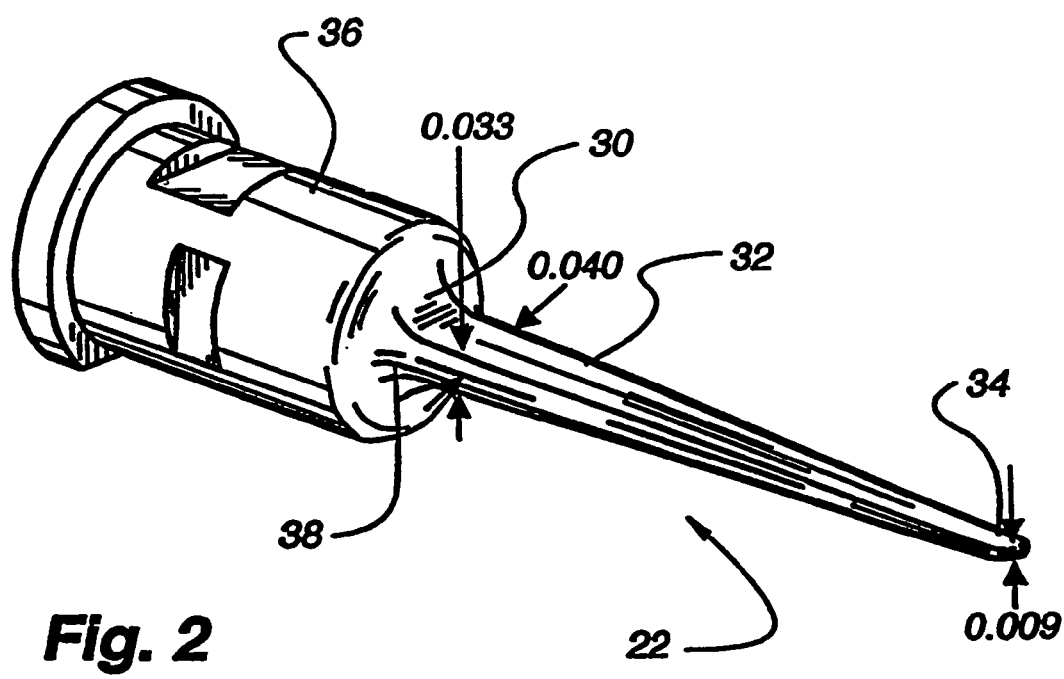
FIG. 2 illustrates an isometric view of a tip for a power dental flossing device, in accordance with one embodiment of the present invention.
Figure 4:
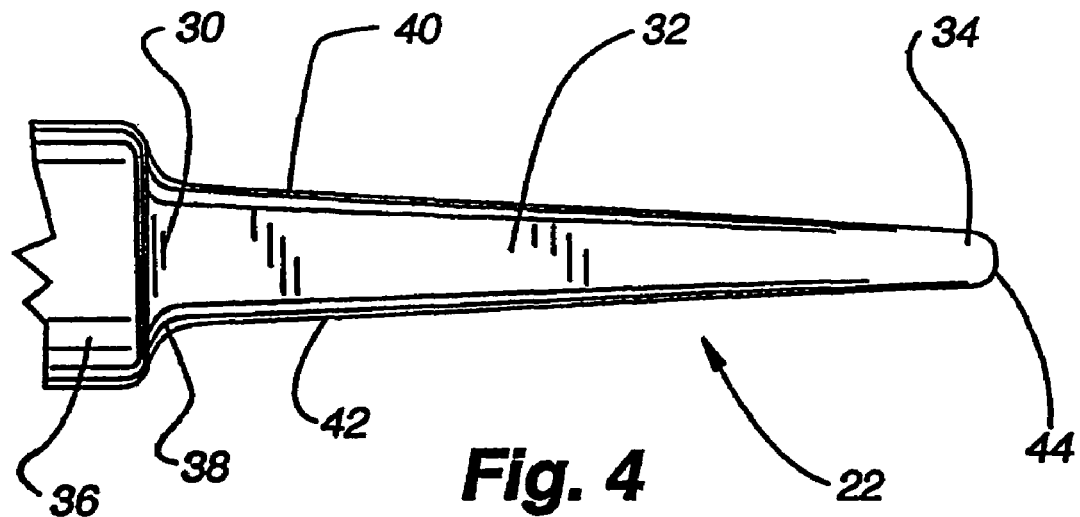
FIG. 4 illustrates a side view of the tip of FIG. 2, in accordance with one embodiment of the present invention.

Referring now to FIGS. 2 and 4, in accordance with the present invention, the flossing tip 22 is an elongated member and includes a base portion 30, a central portion 32, and an end portion 34. The base portion 30 is attached to a connector portion 36, which is adapted to removably attach to an end of the power dental flossing device 20. In one example, the base portion 30 includes a fillet 38 having a generally triangular cross-section. The fillet 38 extends around the perimeter of the base portion and attaches the base portion 30 to the connector portion 36. The base portion 30 and the fillet 38 assist to distribute the stresses incurred along the tip 22 during use, and provide a solid foundation for supporting and connecting the tip 22 to the power dental flossing device 20 through the connector portion 36. In one example, the base portion 30 shown in FIGS. 2 and 4 has a length of approximately 0.026 inches from the connector portion to the top of the fillet 38.

Figure 3:
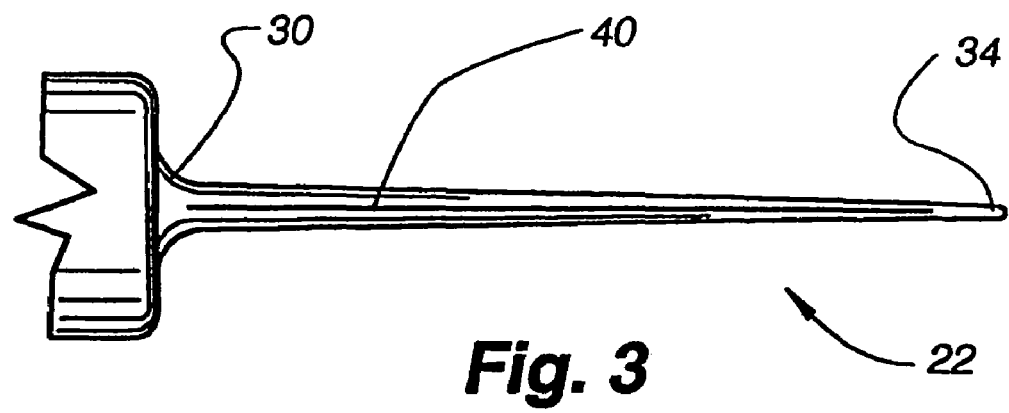
FIG. 3 illustrates a top view of the tip of FIG. 2, in accordance with one embodiment of the present invention.
Figure 7:
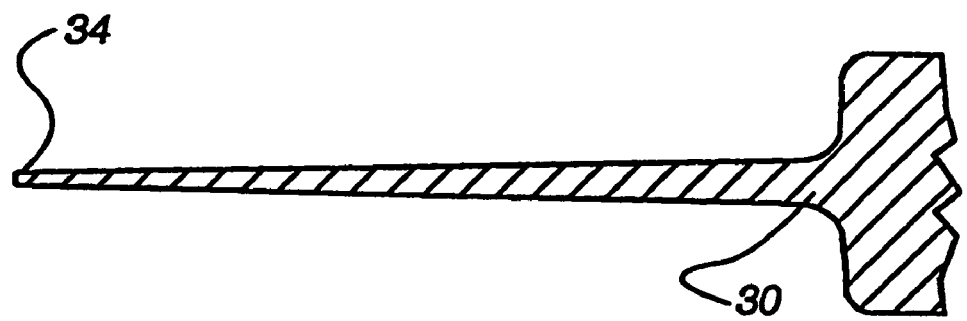
FIG. 7 illustrates a sectional view of the tip taken along section lines 7—7 of FIG. 6, in accordance with one embodiment of the present invention.

The central portion 32, which extends between the base portion 30 to the end portion 34 of the tip 22, has a top and bottom surface 40, 42 which define a width and height dimension. Referring to FIGS. 3 and 7, the width of the top surface 40 decreases along the length of the central portion 32 from the base to the end portion 34. In one example, the width is approximately 0.027 inches proximate the base portion 30, and the width is approximately 0.006 inches proximate the end portion 34. Preferably, the bottom surface 42 of the central portion 32 is substantially identical, in dimensions and shape, to the top surface 40; although the top and bottom surfaces may have different widths at any point along the tip thereby forming an angular cross-sectional profile, if desired. The length of the central portion 32 is approximately 0.51 inches in one example.

Alternatively, the tapering of the top and bottom surfaces 40, 42 can begin after a certain distance (for example, approximately 0.180 inches) along the length of the central portion 32, thereby increasing the mass of the tip proximate the base, which imparts greater strength to the entire tip.

Figure 6:
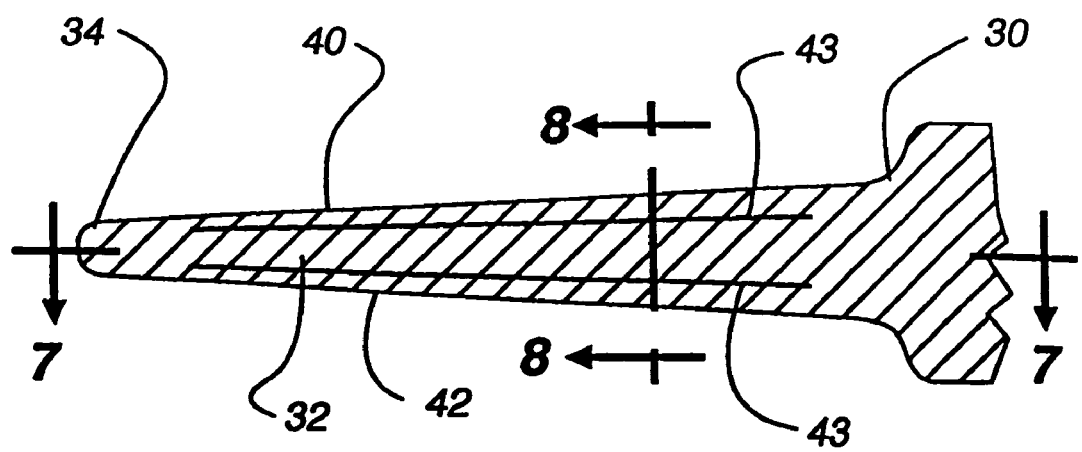
FIG. 6 illustrates a sectional view of the tip, in accordance with one embodiment of the present invention.

Referring to FIGS. 4 and 6, the top and bottom surfaces 40, 42 of the central portion 32 also define a height dimension that decreases along its length, being a maximum at the base 30 and a minimum at the end portion 34. Preferably, the central portion 32 has a height of approximately 0.077 inches proximate the base portion 30, and has a height of approximately 0.031 inches proximate the end portion 34.

Since the width of the top and bottom surfaces 40, 42 decreases along the length of the tip 22 from the base portion 30 to the end portion 34, and the height of the tip likewise decreases, these decreasing dimensions form a flossing tip which is easily slidably inserted between adjacent teeth, while also providing a flossing tip which maintains its orientation once inserted between the adjacent teeth. When the user has finished flossing between a pair of adjacent teeth, the tip is also easily removed from between the teeth due to these decreasing dimensions.

Further, in one example, the top and bottom surfaces 40, 42 of the central portion 32 can be embedded with thin strips 43 of reinforcing material such as metal, spring steel or the like, so as to increase the strength and durability of the tip while maintaining the resilient, flexible nature of the tip. One or more strips 43 are preferably encased in the material of the tip to protect the user's teeth and gums against contact with the strip. However, certain types of materials can be used for the strip 43 to avoid this effect.

Alternatively, a core made of stainless steel, or other reinforcing material, can be embedded within the central portion of the tip to increase the strength and durability of the tip while maintaining the resilient, flexible nature of the tip. The core has a shape generally similar to the central portion, but with smaller dimensions. In one example, the core is approximately 0.475 inches in length. Proximate the base end of the core, the core has a height of approximately 0.025 to 0.030 inches, and a thickness of approximately 0.010 inches. Proximate the end portion, the core has a height of approximately 0.008 to 0.010 inches, and a thickness of approximately 0.003 inches.

Figure 5:
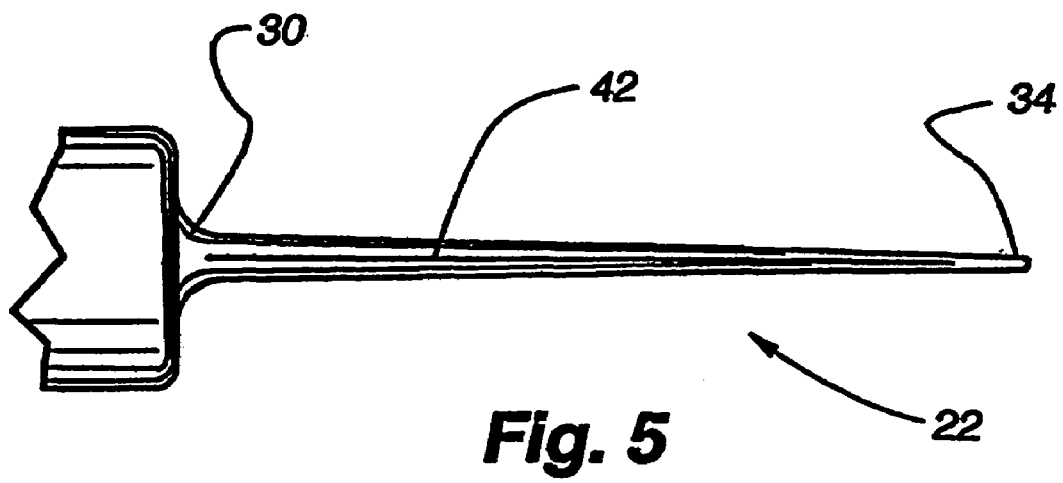
FIG. 5 illustrates a bottom view of the tip of FIG. 2, in accordance with one embodiment of the present invention.

The central portion 32 transitions to the end portion 34 of the tip 22. Referring to FIGS. 4 and 5, the end portion 34 is generally flat along its sides and is rounded, which assists the user in guiding the tip properly within the interproximal space between adjacent teeth, and reduces trauma to the gums. Referring to FIG. 4, the end portion 34 has a rounded or curved end 44, in one example, having a radius of curvature of approximately 0.02 inches. As mentioned above, the end portion has a width along its top and bottom surfaces of approximately 0.006 inches, and a height of approximately 0.031 inches, preferably. The end portion could have other shapes also, but the curved shape is desired for easily guiding the tip between teeth and for being comfortable, and reduces trauma to the gums.

Figure 10:
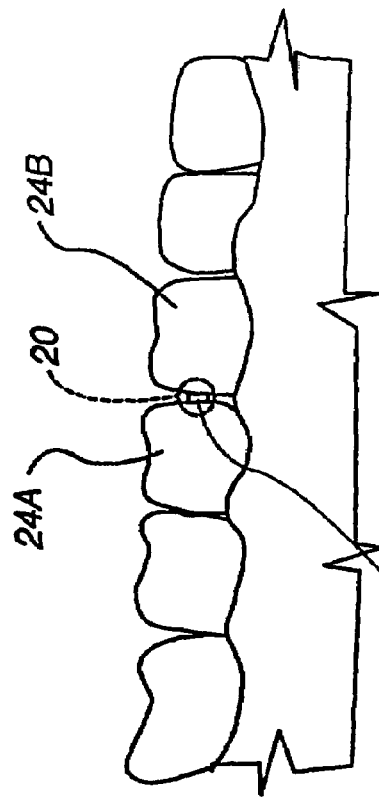
FIG. 10 illustrates a power dental flossing device with a tip in accordance with one embodiment of the present invention, inserted between a pair of adjacent teeth during use.

Referring to FIGS. 9–11, as the tip 22 is slid between adjacent teeth, the end portion 34 of the tip 22 assists in dislodging food particles therein, and the sides 46, 48 of the tip 22 press against the sides 50, 52 of the adjacent teeth 24A, 24B which aligns the tip between the teeth as the tip is slid between the teeth. The distance, which the tip 22 needs to be inserted between the teeth for alignment to occur, will depend on the particular distance between the teeth 24A, 24B and the space between the teeth and gums of a user. Since the gap between teeth is generally a vertical slot, once a sufficient amount of the central portion 32 of the tip 22 has been inserted between the teeth, the tip is aligned therein. Since the tip 22 is made of resilient flexible material, the tip 22 of the present invention generally maintains its alignment between the teeth, as can be seen in FIGS. 9 and 11, even if the handle of the power dental flossing device 20 is slightly moved or slightly rotated (which may mis-align a conventional tip thereby generally decreasing the effectiveness of cleaning).

Figure 8:
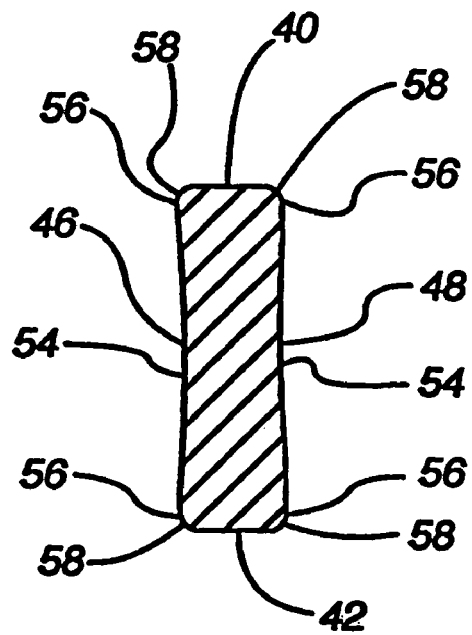
FIG. 8 illustrates a sectional view of the tip taken along section lines 8—8 of FIG. 6, in accordance with one embodiment of the present invention.

As shown in FIGS. 8 and 11, the cross-sectional geometry of the tip 22, at a section taken about the central portion 32, generally forms a rectangle in one example, defined by the top and bottom surfaces 40, 42 and the sides 46, 48 of the central portion 32. Preferably, the sides 46, 48 of the central portion 32 are longer than the width of the top and bottom surfaces 40, 42, which permits at least one side of the tip 22 to engage at least one side of a tooth during use. Preferably, the sides 46, 48 of the tip are curved inwardly towards one another, with a radius of curvature being approximately 0.20 inches in one example. The curve can have a variety of shapes, such as a simple curve or a complex curve, preferably a simple curve.

Referring to FIG. 8, a neck 54 is formed at the point where the tip has its narrowest thickness along the curved sides 46, 48. In one example, the neck 54 is formed along the curved sides 46, 48 at a midpoint between the top and bottom surfaces 40, 42 of the tip 22. Preferably, the neck 54 has a thickness of approximately 0.02335 inches at a point proximate the base portion 30; and a thickness of approximately 0.00587 inches proximate the end portion 34 of the tip. The varying thickness of the neck 54 along the length of the tip assists a user in guiding the tip between adjacent teeth, while providing a tip, which is usable for flossing between teeth having various inter-proximal distances therebetween. The substantially rectangular cross-section also helps impart strength to the entire tip.

The curved sides 46, 48 help to improve the cleaning efficiency by improving the contact area between the sides 46, 48 of the tip 22 and the sides of the teeth. As can be seen in FIGS. 8 and 11, each curved side 46, 48 provides at least two points of contact 56 with a side of each tooth being flossed variously during the flossing process. During flossing, in one example, the tip compresses inwardly from the sides as the tip is moved between teeth, so that the tip can move into and through spaces narrower than the distance between the contact point on the top or bottom edge, respectively. The cross-sectional geometry of the tip shown in FIGS. 8 and 11 is preferably generally rectangular with inwardly curved sides, because such a structure is easily manufactured and provides a strong cross-sectional structure, which is also resiliently compressible. Other shapes, such as I-beam shaped, dog-bone shaped, or oval-shaped, are also feasible for providing indented or inset side walls.

Figure 12:
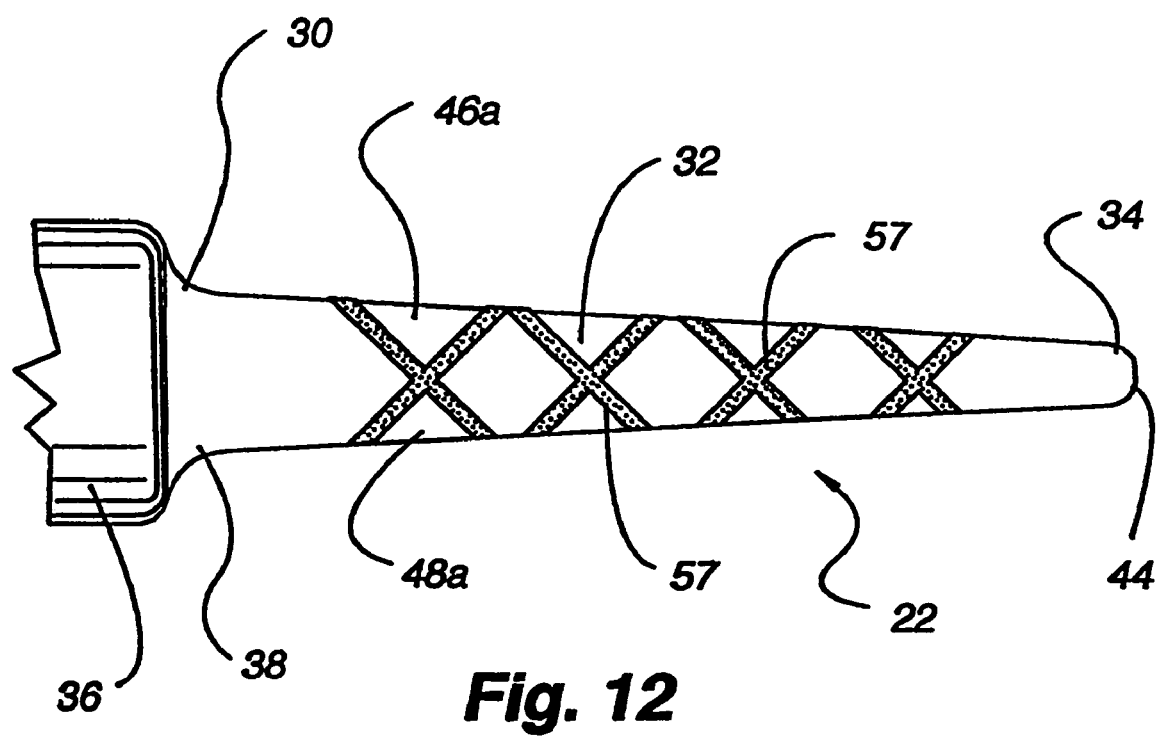
FIG. 12 illustrates a side view of an alternative embodiment of the tip of FIG. 2 of the present invention, where the tip has a surface treatment thereon.

In an alternative embodiment as shown in FIG. 12, sides 46a, 48a have a surface treatment 57, such as a crosshatching pattern, thereon. The surface treatment 57 generally helps improve the cleaning effectiveness of the tip by providing a plurality of gripping edges along the length of the tip to help break down plaque. In one example, the surface treatment 57 is formed on the sides of the tip by etching or cutting thin grooves or ridges or indentations in the sides 46a, 48a. Alternatively, a set of ribs or protrusions can be formed along the sides 46a, 48a, in a crosshatch or other pattern, to form the surface treatment 57. The protrusions can be made, for example, by etching thin grooves or ridges in the mold cavity of the tip. While a crosshatch surface treatment 57 is shown, other surface treatments using different patterns or different densities of the pattern, may be used to improve the cleaning effectiveness of the tip.

The edges 58 of the tip, as shown in FIGS. 8 and 11, are preferably rounded which help prevent damage or injury to the gums of a user upon incidental contact with the tip 22 during use.

During use and referring to FIGS. 9, 10, and 11, the flossing tip 22 of the present invention, being coupled to a power dental flossing device 20, is inserted by the user between adjacent teeth 24A, 24B and the gum line. The end portion 34 of the tip 22 can dislodge any food particles embedded between the adjacent teeth. As the tip 22 is inserted deeper between the adjacent teeth, the curved sides 46, 48 of the central portion 32 of the tip engage the sides 50, 52 of the teeth. As the power dental flossing device 20 is activated and the tip 22 moves linearly, preferably vertically upwardly and downwardly, the contact points 56 of the tip, along with portions of the curved sides 46, 48 of the tip, rub against the sides 50, 52 of the teeth 24A, 24B to break up plaque and provide a dental cleaning action. The contact points move up and down in the space between the teeth to clean the sidewalls of the teeth. Since the tip is resiliently compressible, the contact points at the top and bottom edges of the tip can compress and extend to fit the differing dimensions of the gap to maintain contact. The user can move the tip to contact and clean different portions of the sides of the teeth, and the tip will generally maintain the proper orientation with respect to the teeth to continue to provide an effective dental cleaning action.

Another embodiment of the present invention includes a flossing tip 22 having an enlarged end portion 70 as illustrated in FIGS. 13–18. With exception of the end portion 70, the flossing tip 22 including an enlarged end portion 70 is substantially similar to the flossing tip 22 illustrated in FIGS. 2–8. However, the enlarged end portion 70 provides enhanced cleaning, guidance, and gum protection in the area of use. The enlarged end portion 70 extends in a relative vertical direction (the same direction as the motion of the tip 22 and the orientation of the interproximal space), and not in the lateral direction. The enlarged end portion 70 tapers to its leading edge 72 to provide access to tight interdental spaces (the wedge effect). The varying flex characteristics along the length of the tip 22 gives the user control over the application force of the tip against the tooth and gum. The length of the tip 22 provides access to the full depth of the interdental space, as measured from the outside of the gum (cheek) to the inside of the gum (tongue side), and also allows access into the spaces between the teeth and surrounding gums.

Figure 13:
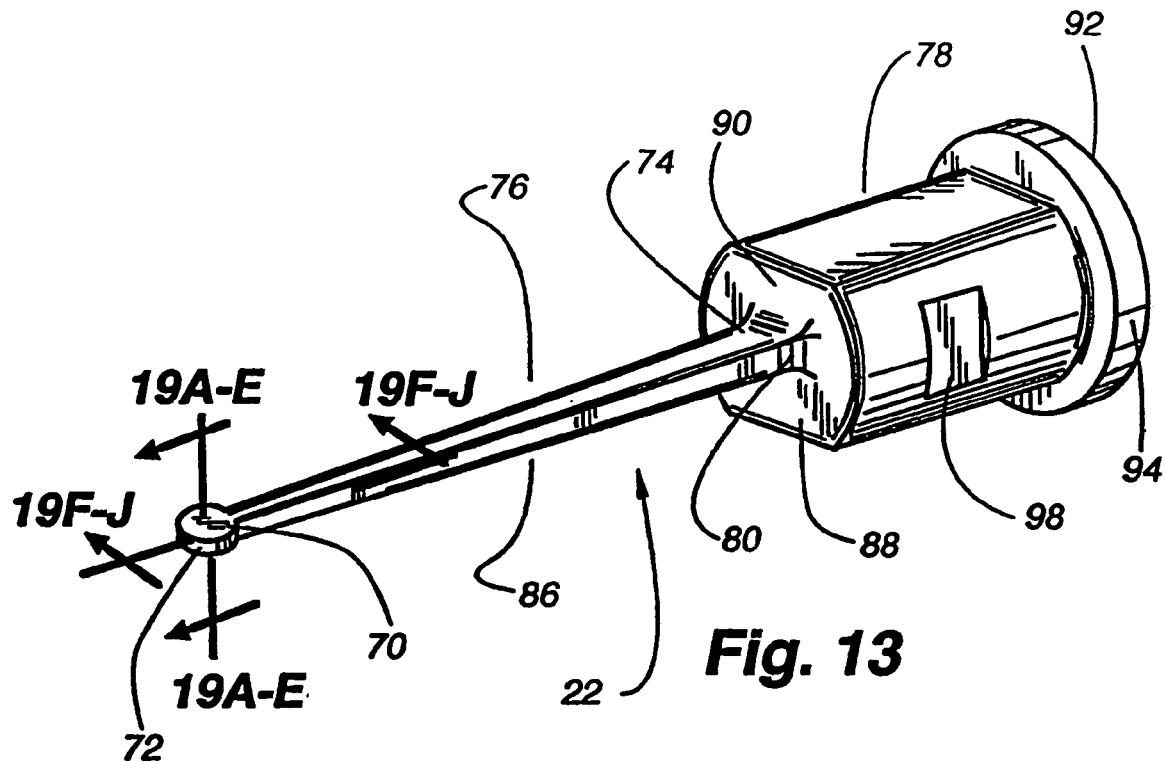
FIG. 13 is a front isometric view of a tip for a power dental flossing device, in accordance with one embodiment of the present invention.
Figure 14:
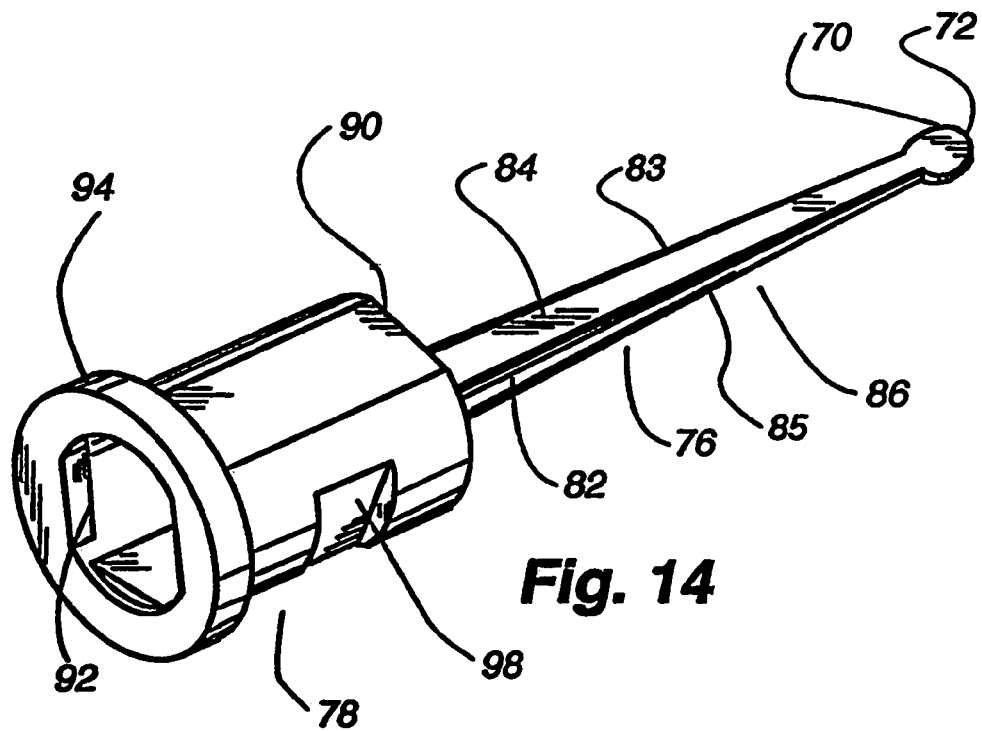
FIG. 14 is a rear isometric view of the tip of FIG. 13, in accordance with one embodiment of the present invention.
Figure 15:
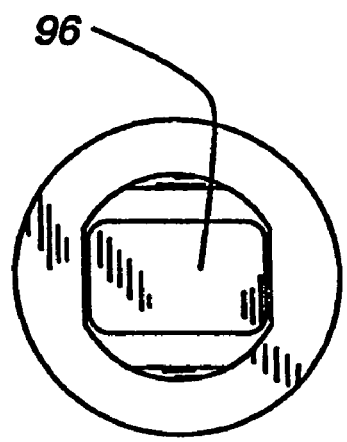
FIG. 15 is a rear view of the tip of FIG. 13, in accordance with one embodiment of the present invention.

Referring to FIG. 13–14, the flossing tip is generally an elongated member and includes a base portion 74, a central portion 76, and an enlarged end portion 70. The base portion 74 is attached to a connector portion or tip connection structure 78, which is adapted to removably attach to the end of a power dental flossing device.

In the embodiment illustrated in FIG. 13, the base portion 74 includes a fillet 80 having a substantially rectangular cross-section. The fillet 80 extends around the perimeter of the base portion 74 and attaches the base portion 74 to the connector portion 78. The base portion 74 and the fillet 80 assist to distribute the stresses incurred by the flossing tip 22 during use, and provide a solid foundation for supporting and connecting the flossing tip 22 to the power dental flossing device through the connector portion 78.

Figure 16:
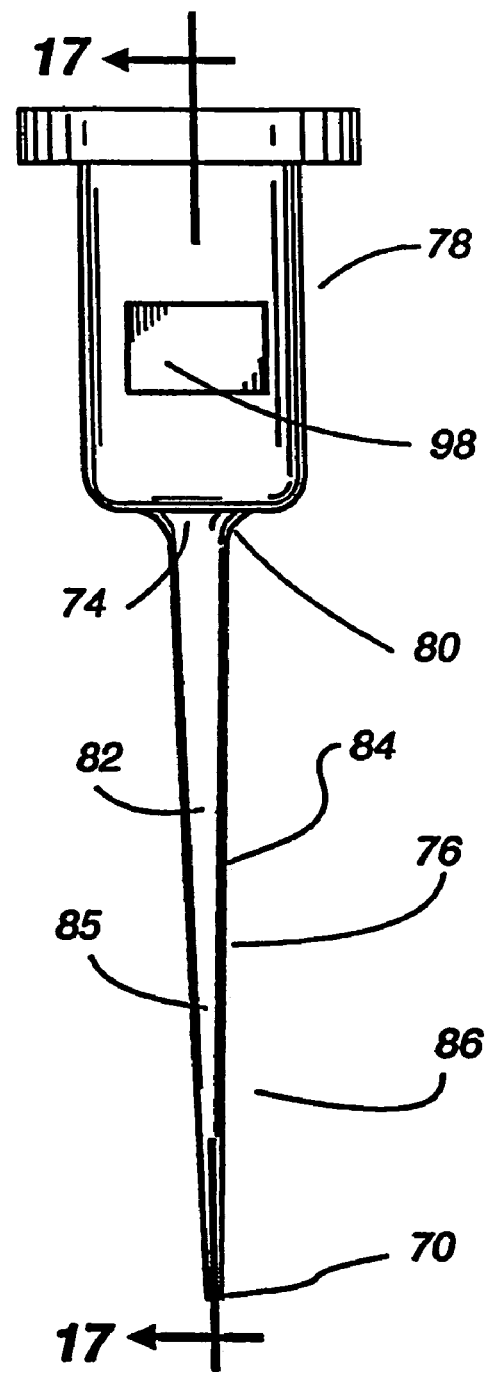
FIG. 16 is a top view of the tip in FIGS. 13–15, in accordance with one embodiment of the present invention.
Figure 17:
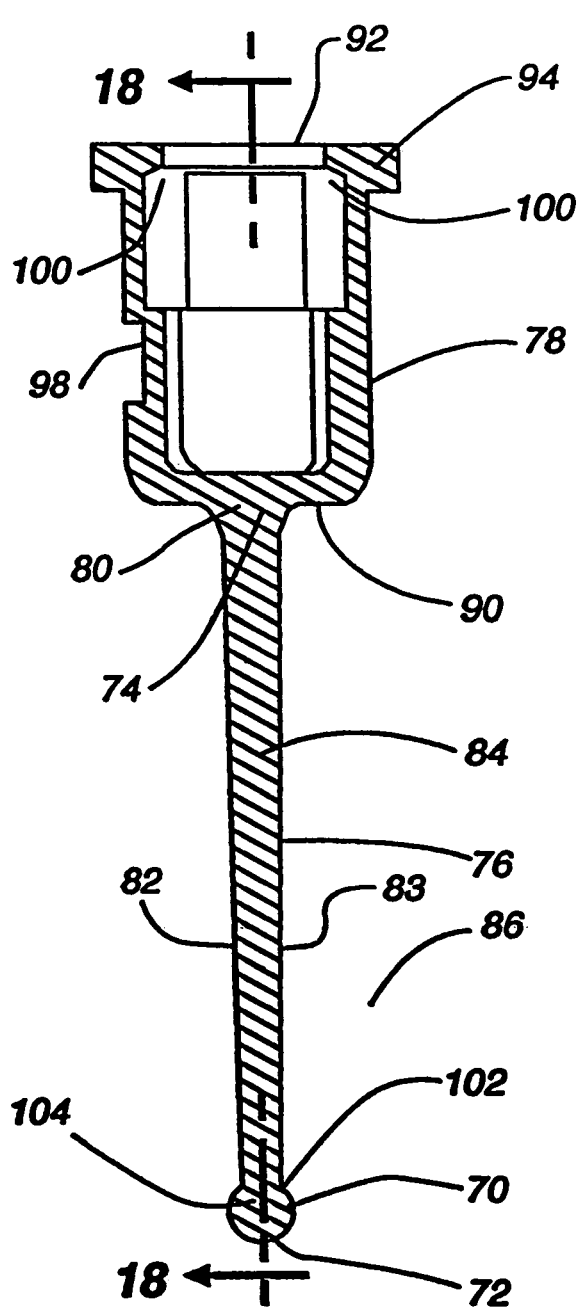
FIG. 17 is a section view of the tip taken along line 17—17 of FIG. 16.

The central portion 76, which extends between the base portion 74 to the end portion 70 of the flossing tip 22, has top and bottom surfaces 82, 83 which define a width and height dimension. Referring to FIGS. 16 and 17, the width of the top surface 82 decreases along the length of the central portion from the base through the end portion. Preferably, the bottom surface 83 of the central portion 76 is substantially identical, in dimensions and shape, to the top surface 82; although the top 82 and bottom 83 surfaces may have different widths at any point along the tip thereby forming an angular cross-sectional profile, if desired.

Referring to FIGS. 14 and 17, the top and bottom surfaces 82, 83 of the central portion 76 also define a height dimension of sides 84 and 85 that decreases along its length, being a maximum at the base 74 and a minimum at the end portion 70. Preferably, the central portion 76 has a height of approximately 0.077 inches proximate the base portion 74, and has a height of approximately 0.031 inches proximate the end portion 70.

Alternatively, the tapering of the top 82 and bottom 83 surfaces can begin after a certain distance along the length of the central portion, thereby increasing the mass of the tip 22 proximate the base 74, which imparts greater strength to the entire tip 22.

FIGS. 13–18 also illustrate the specific detailed structure of the flossing tip. The flossing tip includes a tip connection structure 78 from which extends the flossing element 86. The flossing element 86 and tip connection structure 78 are made of a plastic. The flossing element 86 extends from the center of the end 88 of the tip connection structure 78 and can be straight, curved, or angular, or a combination of any of these. The flossing element 86 is sized to be received in the interproximal spaces. The flossing element 86 may have a pointed end, a disk-shaped end, or any other shaped end sized to be received in the interproximal spaces. Further details regarding the design of the flossing tip 22 are provided in U.S. patent application Ser. No. 09/636,488, filed 10 Aug. 2000, which is hereby incorporated by reference in its entirety.

The tip connection structure 78 has a cup-like shape forming a cavity with a closed end 90 from which the flossing element 86 extends and an open end 92, which receives the top end portion of a flossing device rocker arm 150. The interior of the tip connection structure 78 cavity forms a tip connection structure for releasably securing the flossing tip 22 to the top end of the flossing device rocker arm 150. Adjacent the closed end, diametrically opposed recesses 100 are formed on the interior wall of the tip connection structure 78. The purpose of the latching recesses 100 will be described in greater detail below. The tip connection structure 78 is typically generally cylindrical, but can be deformed to an oval shape as described below. The open end 92 and cavity of the tip connection structure 78 form a rectangular aperture 96 allowing the tip 22 to be mounted one of two ways on the end of the rocker arm 150. The open end 92 of the tip connection structure 78 extends radially outward to form a rim 94 on the open end 92 of the tip connection structure 78. The exterior of the tip connection structure 78 is generally smooth and includes one production indentation 98 that is not related to the functioning of the flossing tip 22. The flossing tip 22 is removed and stored by utilizing a means to engage the tip connection structure 78 rim 94. Further details regarding the removal and storage of the flossing tips 22 and the design of a tip connection structure are provided in U.S. Provisional Patent Application No. 60/148,915, filed 13 Aug. 1999, and U.S. patent application Ser. No. 09/636,488 filed 10 Aug. 2000, which are hereby incorporated by reference in their entirety.

In operation, the enclosed latching recesses 100 in the tip connection structure 78 engage the latching tabs 152 of the mechanism (the top end portion of the rocker arm) to hold the tip 22 in place. The means to engage and disengage the tip 22 are to compress the sides of the tip connection structure 78 and deform it into essentially an elliptical shape. This would create a major axis of an ellipse, which would be larger than the distance across the latching tabs 152 on the top end portion of the rocker arm 150. There is a gap on either side of the top end portion of the rocker arm 150 when inserted in the tip connection structure 78 to allow the tip connection structure 78 to be squeezed to form an elliptical shape. The tip connection structure 78 can deform to an ovalized or non-circular shape to release the latch tabs 152 from the latch recesses 100.

This detent-style tip connection allows for secure placement of the flossing tip 22 on the top end of the rocker arm 150 yet also allows for convenient removal of the flossing tip 22 from the top end portion of the rocker arm 150. The tip connection structure 78 is slidingly engaged over the top end portion of the rocker arm 150 so that the tip connection structure 78 is gradually increased in size to allow the rocker arm latch tabs 152 to seat in the tip connection structure 78 latching recesses 100. The tip connection structure 78 is sufficiently resilient to rebound to its circular shape and thus hold the tip 22 on the top end portion of the rocker arm 150.

When the flossing tip 22 is positioned on the top end of the rocker arm 150, an audible "click" is heard when the flossing tip 22 is correctly seated thereon. This is a positive feature for assuring the user that the flossing tip 22 is firmly attached to the device.

The one area of concern is that when the flossing tip 22 is ejected from the production mold or the tip sides are compressed to unlatch the tip 22, the sides of the tip at 90 degrees to the detent and latch features may tend to yield and stay in a somewhat elliptical shape. This is not so critical when removed from the device since the tip 22 is designed and intended for one use only. However, if it is distorted when it is ejected from the mold during the manufacturing, its latching ability could be severely affected. The material selected for the tip 22, preferably Dupont Zytel™ 101L, or the like, such as NC010 (nylon 66), is believed to overcome this problem.

At the transition point from central portion 76 to end portion 70, hereinafter referred to as the neck 102, the edge of the end portion 70 extends radially outward to define an enlarged end portion 70. The embodiment illustrated in FIGS. 13, 14 and 17 includes an enlarged end portion 70 having a disk shape. In a particularly preferred embodiment, the overall length of the flossing tip 22 is about 0.5 inches, the cross-sectional height dimension ranges from about 0.040 inches at its tallest point to about 0.018 inches at its shortest point, the cross-sectional width dimension ranges from about 0.033 inches at its widest point to about 0.009 inches at its narrowest point (leading edge 72 of the tip), and the disk diameter is about 0.038 inches.

The width of the top 82 and bottom 83 surfaces decreases along the length of the flossing tip 22 from the base portion 74 through the end portion 70, and the height of the flossing tip 22 then decreases from the base portion 74 to the end portion 70, and the height of the flossing tip 22 increases along the enlarged end portion 70. These dimensions form a flossing tip 22, which is easily slidably inserted between adjacent teeth and between gums and teeth, while also providing a flossing tip 22 which maintains its orientation once inserted between the adjacent teeth. In addition, the enlarged end portion 70 increases the user's comfort by reducing trauma to the gums. Aside from enhancing comfort levels, the enlarged end portion 70 also increases flossing efficiency by providing additional cleaning edges (at least on the top and bottom). When the user has finished flossing between a pair of adjacent teeth, the tip 22 is also easily removed from between the teeth due to this shape.

Figure 18:
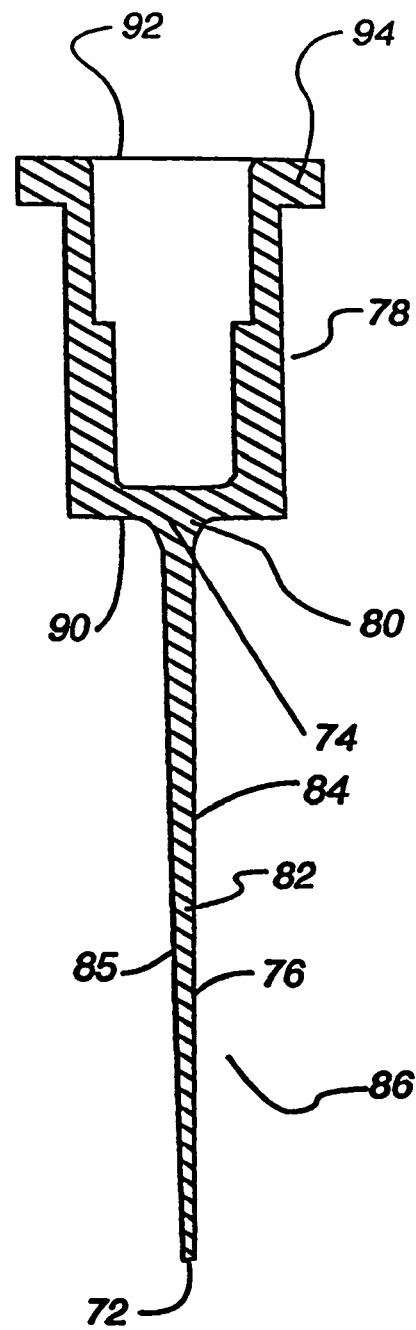
FIG. 18 is a section view of the tip taken along line 18—18 of FIG. 17.
Figure 17A:
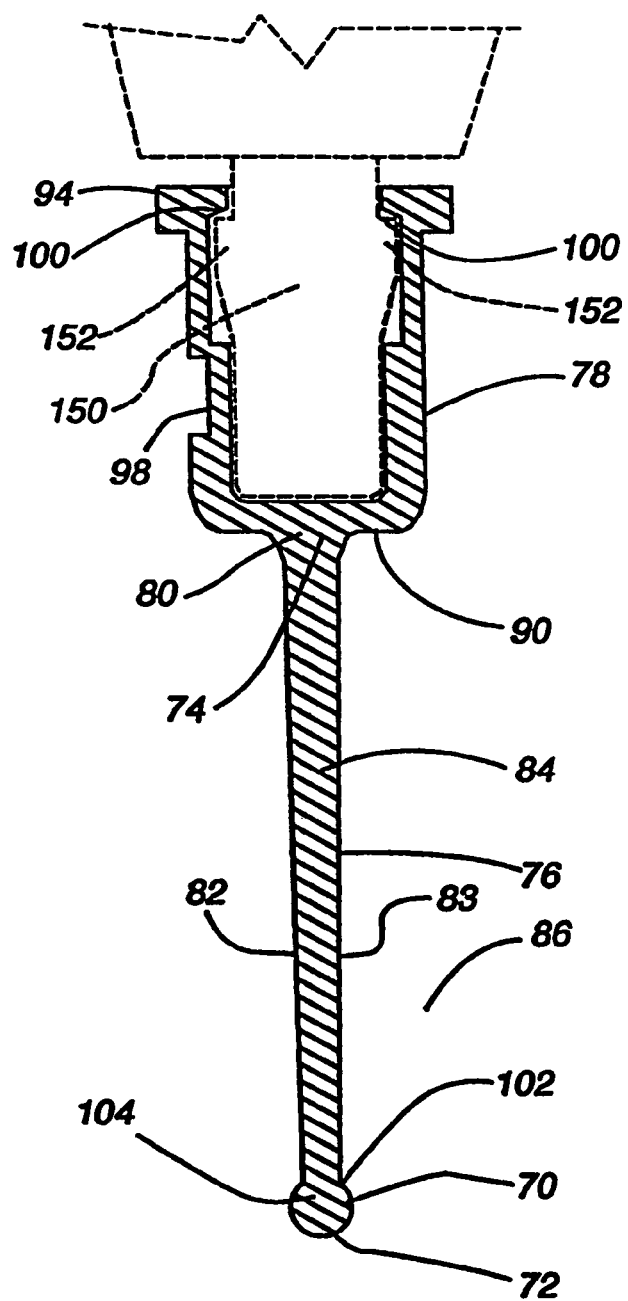
FIG. 17A is the section view of FIG. 17 with a flossing device rocking arm inserted into the tip (in dash).
Figure 18A:
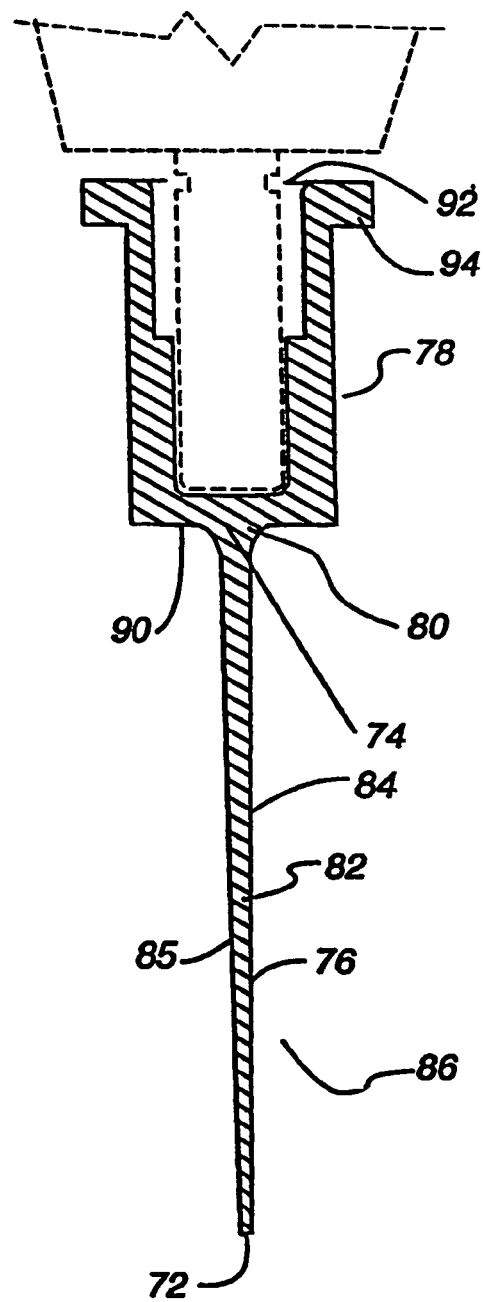
FIG. 18A is the section view of FIG. 18 with a flossing device rocking arm inserted into the tip (in dash).

The central portion 76 transitions to the enlarged end portion 70 of the flossing tip. Referring to FIGS. 13–14 and 17–18, the width of the enlarged end portion 70 decreases from the end of the central portion 76 to the leading edge 72 of the enlarged end portion 70. The leading edge 72 of the enlarged end portion 70 is generally flat, as shown in FIGS. 16 and 18, but can also be smooth and rounded. The height of the enlarged end portion 70 increases radially outward from the end of the central portion to define an enlarged end portion 70 including a rim having a round, disk shape 104. The enlarged end portion 70 assists the user in guiding the tip portion 22 properly within the interproximal space between adjacent teeth, and reduces trauma to the gums. Both the width and height of the disk shape 104 are selected to provide an end portion 70 that easily and comfortably fits between teeth. The end portion 70 could have other shapes also, but the generally flat or tapered disk shape 104 is desired for easily guiding the end portion 70 between teeth, for providing additional cleaning edges, for being comfortable, and for reducing trauma to the gums.

Figure 19A:
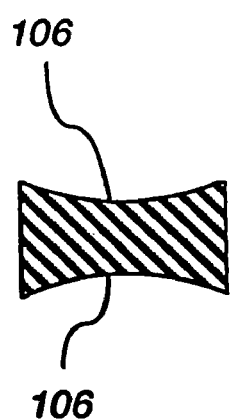
FIGS. 19A–19E are vertical section views taken along line 19AE–19AE of FIG. 13 and FIGS. 19F–19J are longitudinal section views taken along line 19FJ—19FJ of FIG. 13, illustrating alternative embodiments of the present invention.
Figure 19B:
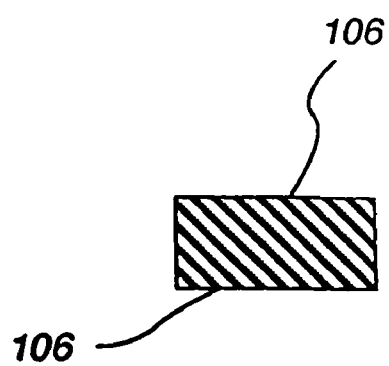
Figure 19C:
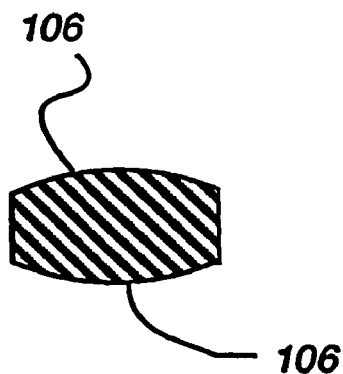
Figure 19D:
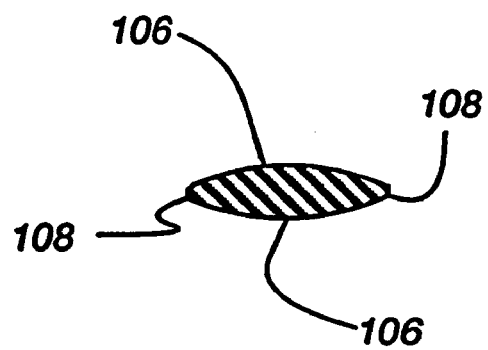
Figure 19E:
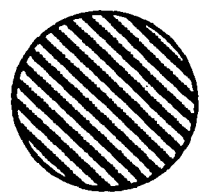

Other embodiments of the flossing tip 22 include flossing tips having enlarged end portions 70 with shapes other than the disk shape 104. In other embodiments, the end portion 70 may include any cross-sectional and/or side view shape providing the dimensions of the end portion are sized to easily and comfortably fit between teeth and between the teeth and gums. FIGS. 19A–19E illustrate vertical section views of alternatively shaped flossing tip end portions taken along the plane transverse to the length of the tip and through the tip end portion. In FIG. 19A, the sidewalls 106 of the tip are concave facing outwardly. In FIG. 19B, the sidewalls 106 of the tip are parallel. In FIG. 19C, the sidewalls 106 of the tip are convex facing outwardly. In FIG. 19D, the sidewalls 106 of the tip convex outwardly, with the top 108 and bottom 110 sides being relatively narrow. In FIG. 19E, the sidewalls of the tip form a continuous circular shape. FIGS. 19F–19J illustrate longitudinal section views of alternatively shaped flossing tip end portions taken along the length of the tip end portion. In FIG. 19F, the end portion 70 is an oblong or oval in a direction transverse to the length of the tip. In FIG. 19G, the end portion 70 is an oblong or oval in a direction in line with the length of the tip. In FIG. 19H, the end portion 70 is an oblong or oval in a direction transverse to the length of the tip, with pointed ends 112. In FIG. 19I, the end portion 70 is square or rectangular. In FIG. 19J, the end portion is pointed. Shapes that both increase the number of cleaning edges and help reduce trauma to the gums are preferred.

During use and referring to FIG. 20, the flossing tip 22, including an enlarged end portion 70, of the present invention is inserted by the user between adjacent teeth 114 at the gum line 116, or between the teeth and surrounding gums. Because the tip 22 is properly oriented in a vertical position, the enlarged end portion 70 of the tip is not discernible in FIG. 20. The end portion of the flossing tip can dislodge food particles embedded between the adjacent teeth, or in the space between a tooth and its surrounding gum. The tip preferably stays relatively straight during use, but can bend to allow for some mis-alignment.

Figure 21A:
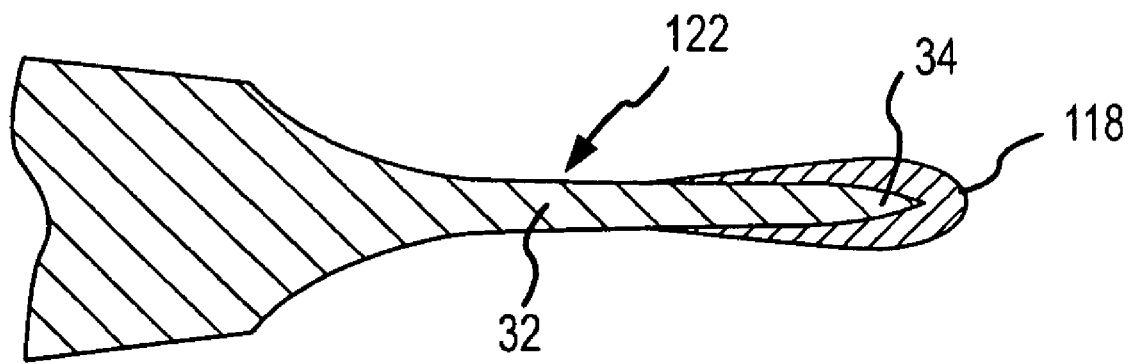
FIG. 21A depicts a representative longitudinal cross-section of a power dental flossing device tip including a whitening compound.
Figure 21B:
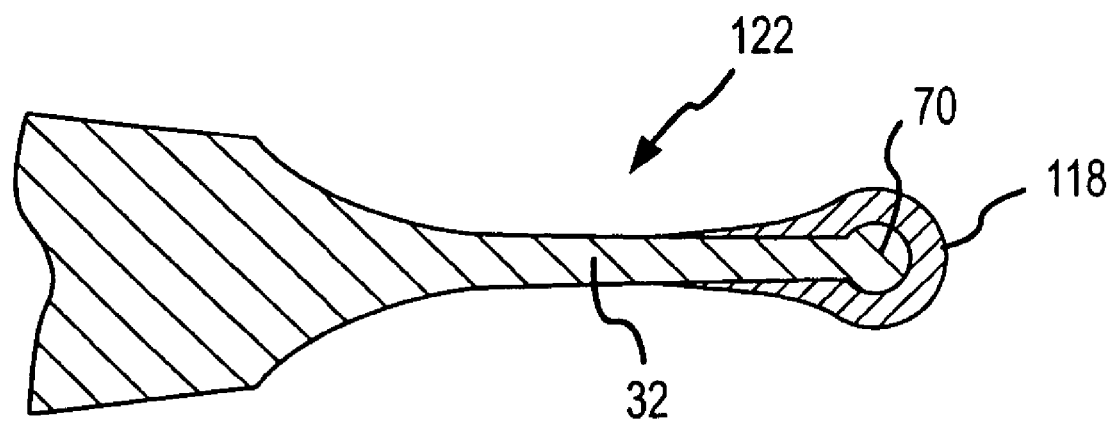
FIG. 21B depicts a representative longitudinal cross-section of a second power dental flossing device tip including a whitening compound.

FIGS. 21A and 21B are representative cross-sectional views of two flosser tips 122 incorporating a whitening compound coating 118, taken along the tip's longitudinal axis. Generally, the coating 118 takes the form of a hardened, abrasive compound distributed about the tip exterior. The compound includes a whitening agent, monomers and prepolymers, a catalyst, a graft initiator, and a flavoring agent. The compound may include additional ingredients, as well. Of course, the whitening compound 118 may be used with any of the aforementioned tip designs and shapes to form a variety of whitening tips suitable for use with a power flossing device 20.

Still with reference to FIGS. 21A and 21B, the whitening compound 118 is generally slightly thicker at the end portion 34, 70 of the tip 122 than at the center portion 32. The whitening compound covers the entirety of the end portion, and extends partway up the center portion in a narrowing fashion. Thus, the compound 118 may present a bulbous shape in cross-section. This is particularly true when the compound is used with a tip 122 having a disk-shaped end portion 70, as shown in FIG. 21B.

In the present embodiment, the compound 118 whitens teeth by rubbing away stains and discolorations. Fine abrasive particles are suspended in the compound. The abrasive particles rub against plaque and other deposits on a tooth surface, shearing and scrubbing them away from the tooth and thus whitening the tooth's overall appearance. The abrasive action is effective not only on front and back tooth surfaces, but also on the sides of the tooth and in other hard-to-reach places. In some embodiments, the compound 118 may contain chemical whitening in addition to, or instead of, the abrasive whitener. The compound 118 may also include antimicrobial chemicals designed to freshen a user's breath or eliminate bacteria that lead to tooth or mouth diseases.

Further, the whitening compound 118 includes a flavoring designed to create a pleasing taste when the tip is placed in a user's mouth. In one embodiment, a mint flavoring is used, although alternate embodiments may employ different flavorings. Other embodiments may omit flavorings entirely.

The compound 118 may be formulated to last for several uses, or may dissolve after a single use. The compound 118 typically reacts to saliva and/or water at room temperature, both activating the compound's whitening properties and dissolving the compound. This reaction causes the whitening compound to form a foam 120 (shown, for example, in FIG. 22B), which not only assists in the removal of tooth stains, but also serves as an effective vehicle for carrying any flavoring added to the compound. By varying the chemical composition of the compound 118, the rate of dissolution may be varied. As a user flosses his or her teeth, the oscillating motion of the flosser tip 122 not only wears down deposits, but also causes the coating 118 to dissolve and wear away. In this manner, the compound becomes ineffective after a desired number of uses. In the present embodiment, the whitening coating is eliminated after a single use of average duration at room temperature.

Figure 22A:
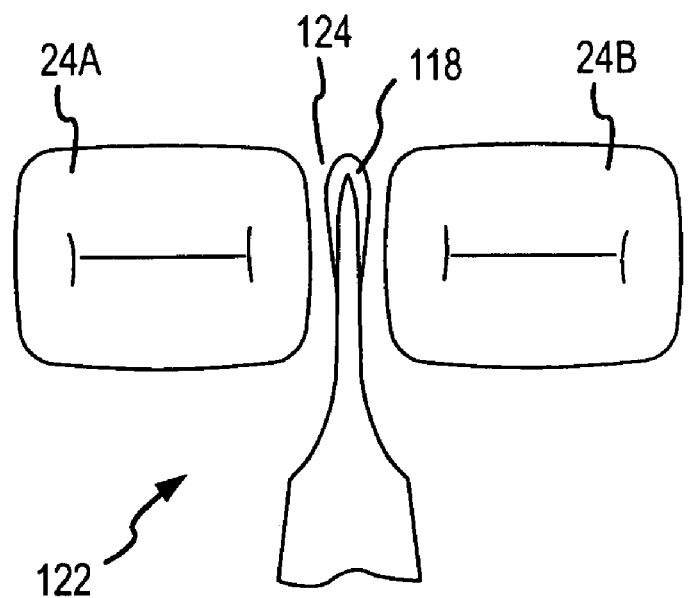
FIG. 22A depicts an inactive power dental flossing device tip including a whitening compound inserted into an interdental space.

Although the coated flosser tip 122 is slightly thicker than a non-coated tip 22, it still may fit comfortably into the interdental spaces 124 between teeth 24A, 24B, as shown in FIG. 22A. When the tip 122 is initially inserted between teeth, the whitening compound generally contacts the side of a tooth. However, the coating 118 remains stable while the flosser is in the "off" position, since minimal saliva and/or water is located between teeth.

Figure 22B:
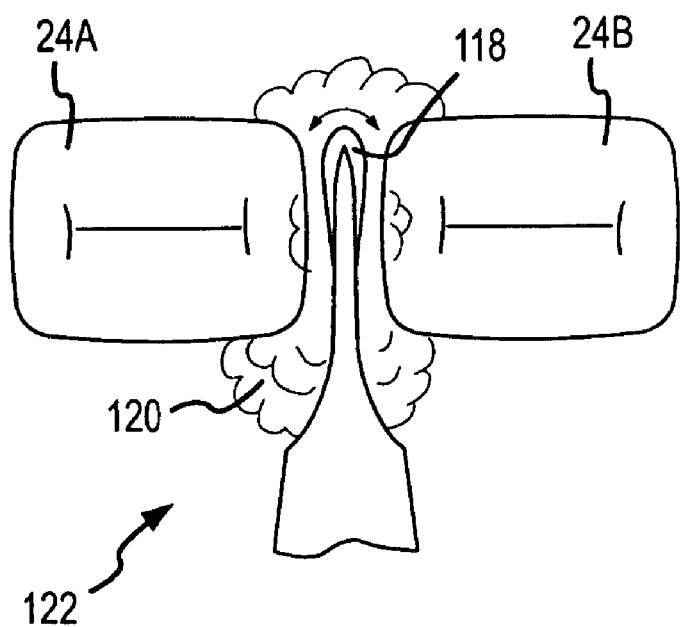
FIG. 22B depicts an operating power dental flossing device tip including a whitening compound inserted into an interdental space.

Once the power flosser 70 (not shown in FIGS. 22A–22B) is turned on, the tip 122 rapidly oscillates, as shown in FIG. 22B. The direction of oscillation is shown by the double-headed arrow. This oscillation brings the whitening compound 118 into contact with greater portions of the teeth surfaces. Accordingly, the compound also contacts the residual saliva left on these surfaces. Further, the oscillating action may stimulate saliva production. The increased amounts of saliva activate the foaming properties of the whitening compound 118, and also induce the aforementioned dissolving of the coating.

The foam 120 may distribute the whitening agent in the compound 118 across a greater surface of the tooth than is contacted solely by the oscillating action of the tip, for example, at least partially filling the interdental space 124. As the foam 120 is agitated by the tip 122 motion, the whitening effect of the compound (whether induced by chemical reaction or abrasive particulates) may occur across portions of the tooth 24A, 24B not directly contacted by the tip.

Although the exemplary tips 122 shown in FIGS. 21A and 21B are primarily intended for use between teeth 24A, 24B, the flosser tips may also be used to clean the front and back surfaces of a tooth, and especially may be used to remove discolorations or deposits therefrom. The oscillating motion of the tip 122, foaming action, and abrasive properties of the whitening compound 118 are all effective on a tooth's front or rear surface. The flosser tip may be oriented either perpendicular or parallel to the tooth surface and still perform its whitening and cleaning functions.

Typically, the whitening compound 118 is chemically attached to a nylon substrate of the flosser tip 122 through a chemical grafting reaction. The grafting reaction covalently bonds the whitening compound 118 to the nylon body of the flosser tip 122. Generally, a graft initiator (GI) having a positive charge begins the reaction. Suitable graft initiators include ferrous or ferric cerium, ferrous ammonium sulfate, ferrous salts, and so forth.

The graft initiator abstracts the hydrogen atom of the nylon amide (CONH) group, forming a free radical site on the nylon substrate. In essence, the amide group is oxidized, while the graft initiator becomes an electrically neutral molecule. Thus, once the initial reaction is complete, the nylon substrate is a highly reactive free radical, the hydrogen atom has a positive charge, and the graft initiator is electrically neutral. The initiation portion of the bonding reaction may be shown as follows:

$$CONH + GI^+ \longrightarrow CON^* + H^+ + GI \qquad 1$$

Once the radical site is formed on the nylon substrate, a monomer is introduced in step 2. The aforementioned whitening compound 118 is attached to the monomer, and is represented (for illustrative purposes only) in the equation below as "X". Once the monomer is introduced to the free radical sites on the nylon substrate, it bonds with the radical site, forming a graft polymer radical. Accordingly, the whitening compound 118 is also bonded to the nylon substrate through the intervening monomer. The radical site on the substrate effectively attacks the double bond between the carbon atoms, as shown in step 2 below, breaking the double bond and forming a covalent bond between the monomer and the nylon substrate. This reaction step converts the CH group on the monomer into a new radical, thus ensuring the bonding may continue as detailed in step 3, below. This permits additional monomers (and thus, additional whitening compound 118) to be bonded to the nylon substrate.

Although a specific monomer is shown in step 2 (specifically, $CH_2=CH$), it should be noted that other monomer compounds may be used to bond the whitening compound 118 to the nylon support. For example, various acrylics or meta-acrylics may be used.

2.
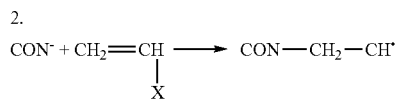

Next, in step 3 the reaction propagates, bonding multiple monomers together to form a polymer chain. Generally, the CH radical breaks the double bond between the $CH_2$ and CH groups in each monomer molecule, forming a series of single bonds linking the former CH radical, the $CH_2$ molecule, and the new CH* radical. This reaction may continue indefinitely, as shown below. The final CH group in the molecule will always be a radical, and thus may continue propagation.

3.
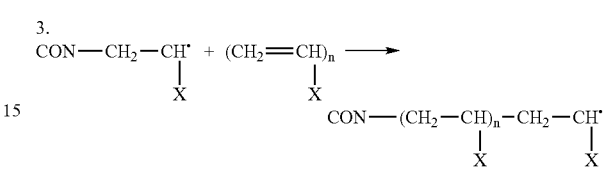

In the present embodiment, the reaction takes place in the presence of a peroxide, represented below as "ROOH." A variety of compounds may be represented by R. In the present embodiment, R denotes a hydrogen peroxide. The peroxide removes an electron from the graft initiator, splitting the peroxide group into a negatively charged oxygen-hydrogen compound and an electrically neutral oxygen radical, while simultaneously regenerating the graft initiator ion. Since the graft initiator is regenerated, it may begin the grafting process anew. This process is shown in step 4, below.

$$ROOH + GI \longrightarrow RO^* + OH^- + GI^+ \qquad 4$$

The reaction may be quenched through radical combination. In step 5, the monomer chain, bonded to the substrate, combines with the oxygen radical formed in step 4. The combination of the oxygen and monomer radicals forms a stable chemical group (CHOR), eliminating both free radicals. Since the resulting molecule lacks a radical to continue propagation, the reaction stops.

5.
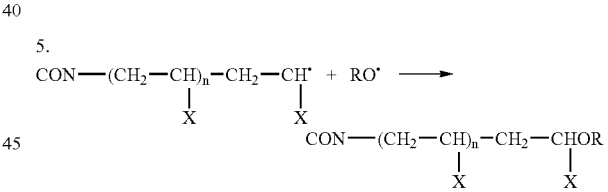

Alternately, two radical monomers (both attached to the flosser tip 122 nylon substrate) may combine. This also quenches the propagation process, as shown in step 6, below.

6.
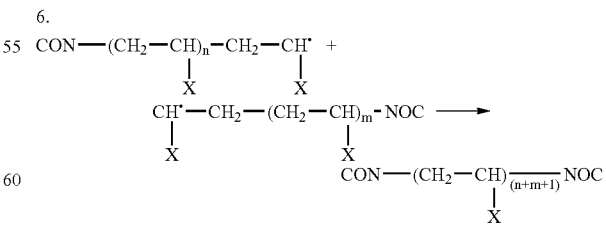

Two different embodiments of the whitening compound 118, as well as related methods of manufacture, are shown below as "Embodiment 1" and "Embodiment 2." The first embodiment includes the listed chemicals in the proportions as described below. Although specific weights are given for each element, the amount of each element may be varied so long as the overall proportions are at least roughly maintained. Immediately following the chemical lists for each embodiment is the method for manufacturing both embodiments of the whitening compound 118.

Embodiment 1

1. Part A

| Chemical | Amount (in grams) |
| --- | --- |
| Neocryl A-1054 | 25.00 |
| deionized water | 10.00 |
| butyl CELLOSOLVE | 5.00 |
| Surfynol 440 (0.1% concentration, diluted in deionized water) | .50 |
| calcium carbonate | .62 |
| Ti O$_2$ 3328 | 7.00 |
| Zeolex 80 | 10.00 |
| Sylodent 700 | 15.00 |
| ferrous ammonium sulfate (0.1% solution) | 0.01 |
| hydrogen peroxide (0.1% solution) | 0.01 |

2. Part B

| Chemical | Amount (in grams) |
| --- | --- |
| polyvinyl alcohol (4% solution in deionized water) | 67.09 |
| sodium benzoate | 0.67 |
| mint flavor 800 U75 (or other flavoring) | 5.36 |
| ferrous ammonium sulfate (0.1% solution) | 0.01 |
| hydrogen peroxide (0.1% solution) | 0.01 |

Embodiment 2

1. Part A

| Chemical | Amount (in grams) |
| --- | --- |
| Neocryl A-1054 | 25.00 |
| deionized water | 10.00 |
| butyl CELLOSOLVE | 5.00 |
| Surfynol 440 (0.1% concentration, diluted in deionized water) | .50 |
| calcium carbonate | .62 |
| Ti O$_2$ 3328 | 7.00 |
| Zeolex 80 | 10.00 |
| Sylodent 700 | 20.00 |
| ferrous ammonium sulfate (0.1% solution) | 0.01 |
| hydrogen peroxide (0.1% solution) | 0.01 |

2. Part B

| Chemical | Amount (in grams) |
| --- | --- |
| polyvinyl alcohol (4% solution in deionized water) | 71.67 |
| sodium benzoate | 0.72 |
| mint flavor 800 U75 (or other flavoring) | 5.73 |
| ferrous ammonium sulfate (0.1% solution) | 0.01 |
| hydrogen peroxide (0.1% solution) | 0.01 |

Part A of each embodiment of the whitening compound 118 is created in the following manner. Initially, the deionized water is mixed with butyl CELLOSOLVE, manufactured by the Dow Chemical Company, or another appropriate drying retardant agent. CELLOSOLVE is one example of an ethylene glycol monobutyl ether; other such compounds may be employed. The resulting mixture is added to Neocryl A-1054, which is one example of a suitable acrylic pre-polymer. Additionally, a wetting agent, such as Surfynol 440 diluted in deionized water, is added. Calcium carbonate, Ti O$_2$ 3328 (or other suitable white filler), and a sodium silicoaluminate or other thickener, such as ZEOLEX 80 (manufactured by J.M. Huber Corp.) is added to the mixture, along with ferrous ammonium sulfate, and hydrogen peroxide. Once all chemicals have been combined, the mixture is milled on a pebble ball mill for approximately twenty-four hours. After milling, the formula is filtered through a polyester filament, such as filament style #718, manufactured by Test Fabrics Co. Generally, the above process is conducted at room temperature and approximately 6.5–7 pH.

Part B of each embodiment of the whitening compound 118 may be manufactured simultaneously with Part A, or while Part A is milling. To manufacture Part B, polyvinyl alcohol is first dispersed in cold or room temperature water. The polyvinyl alcohol should be agitated in order to wet all suspended particles. Next, the alcohol solution is heated to a temperature of approximately 185–205 degrees Fahrenheit (85–96 degrees Celsius). The solution is agitated at this temperature for approximately 30 minutes, after which it is cooled to room temperature.

Once cool, biocide sodium benzoate is added to the solution. The solution should be agitated while the sodium benzoate is agitated. The mint (or other) flavoring is then added, still while agitating the formula. When the formula is sufficiently agitated, it will appear to be an emulsion.

Once emulsified, the final activators are added, namely ferrous ammonium sulfate and hydrogen peroxide. Part B of the whitening compound 118 is now prepared.

Once Part A of the whitening compound 118 has been sufficiently milled and Part B is prepared, an abrasive such as SYLODENT 700 (manufactured by W.R. Grace & Co.) is added to Part A. Part A and Part B may be combined in relatively small portions while mixing at a slow speed in order to thoroughly combine the two solutions. Typically, Parts A and B are mixed together in a ratio of approximately 1.337 (Part A) to 1.0 (Part B), by weight. Alternate embodiments may employ different weight ratios, such as 1:1, 1.25:1, 1.33:1, 1.5:1, and so on. The compound 118 is ready for use when it appears smooth and has no lumps therein. The resulting whitening compound 118 is shown in the grafting reaction above as a "monomer" having the whitening agent "X."

Figure 23:
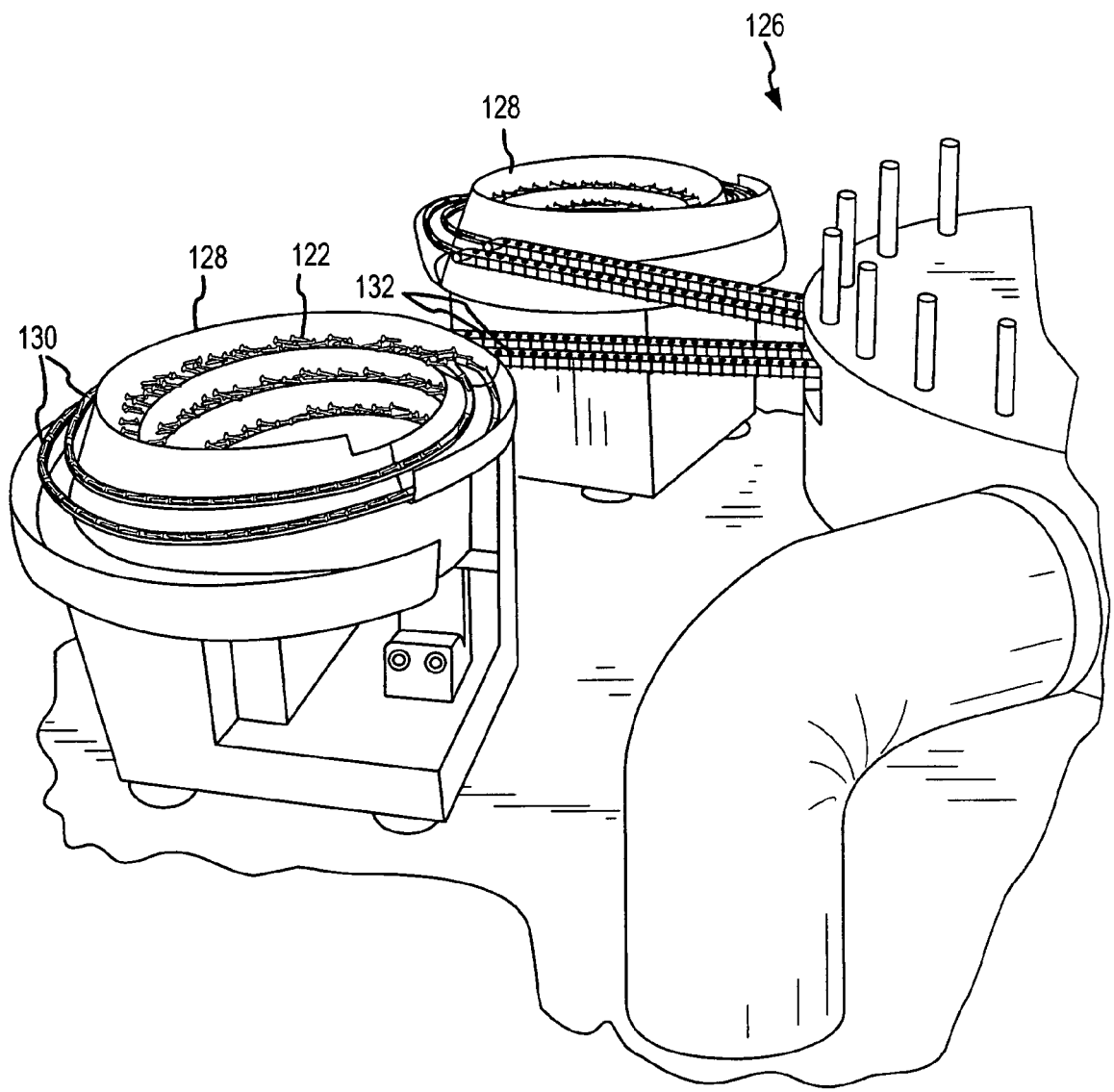
FIG. 23 depicts a first view of an apparatus suitable for coating a power dental flossing device tip with a whitening compound.
Figure 24:
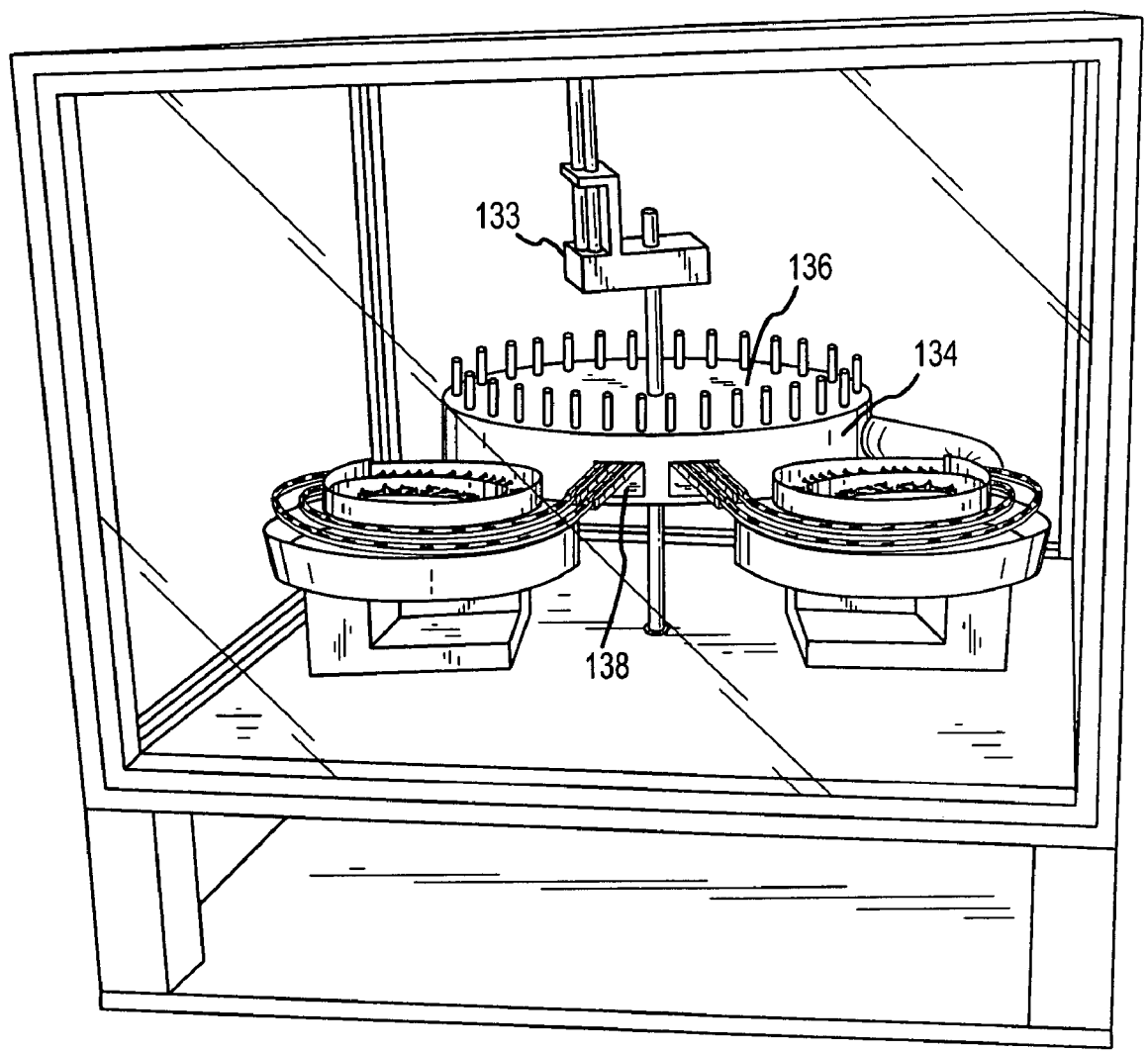
FIG. 24 depicts a second view of an apparatus suitable for coating a power dental flossing device tip with a whitening compound.
Figure 25:
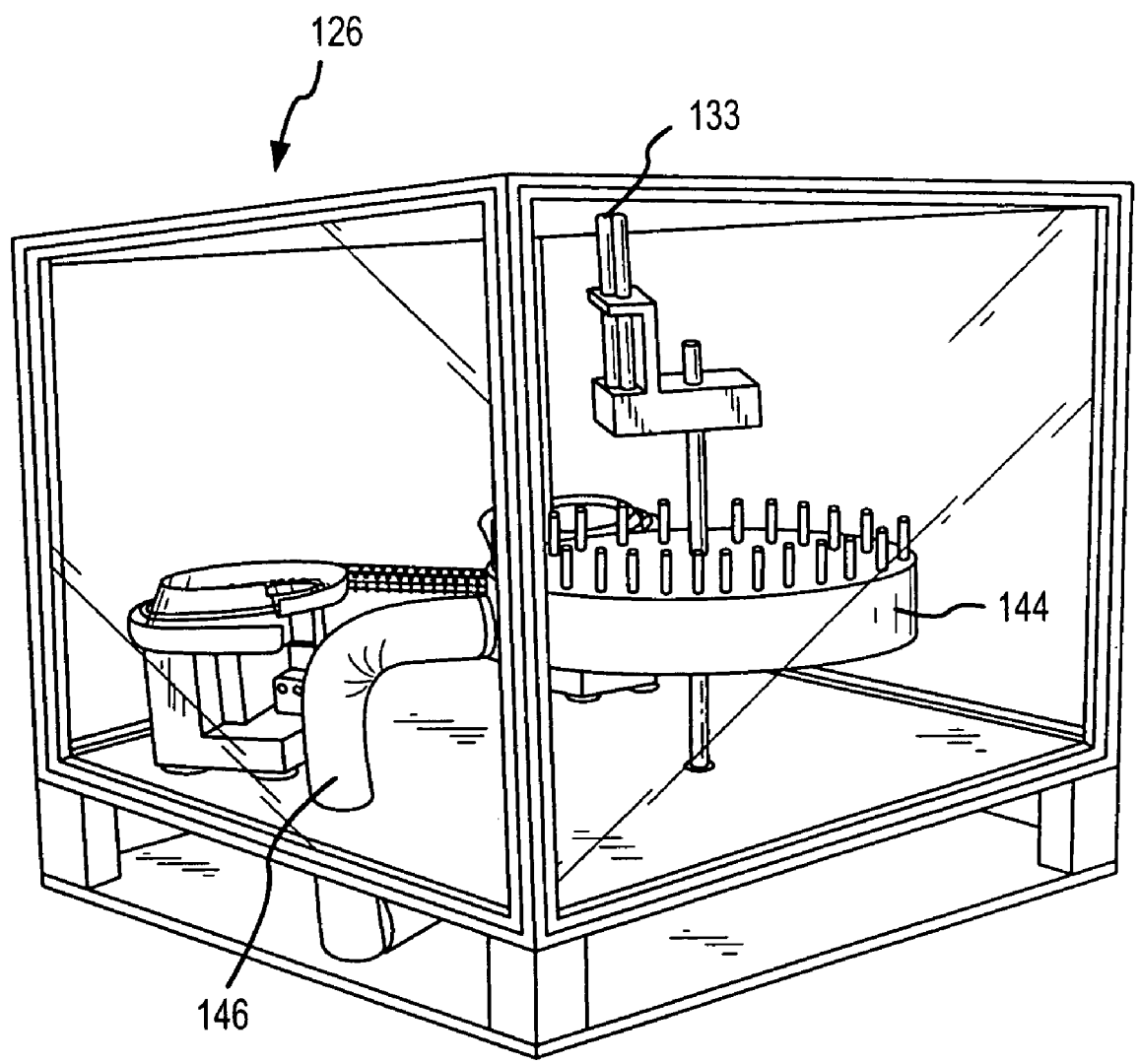
FIG. 25 depicts a third view of an apparatus suitable for coating a power dental flossing device tip with a whitening compound.

FIGS. 23–25 display an apparatus 126 embodying a method of manufacturing whitening tips 122 in accordance with an embodiment of the invention. Referring now to FIG. 23, uncoated tips are loaded into a hopper 128. Each hopper 128 includes a pair of tracks or rails 130 on which the tips are sorted and aligned. Generally, the tips 122 are aligned in two lines, each one tip wide with the tip end facing down, as shown in FIG. 23. The hopper 128 typically rotationally vibrates, which places the tips along one of the spiral tracks 130. The hopper may vibrate more quickly on one side of the hopper bowl than the other, thus imparting motion along the inclined track or rail. The rails 130 may also vibrate in order to impart lateral motion to the tips, and/or align the tips. Once aligned, the tips are carried by two conveyors 132 (per hopper 128) from the hoppers into a covered vat 134, as best seen in FIG. 24. Each conveyor holds a single row of tips. In one embodiment, the conveyors 132 may simply be extensions of the vibrating track or rail 130 previously mentioned. The vat 134 is covered, and the conveyors 132 feed into openings 138 beneath the vat cover 136. Alternate embodiments may employ a different number of tracks, conveyors, hoppers, or vats. For example, an alternate embodiment may include a single hopper 128, three tracks 130 sorting tips 122 from the hopper, and three conveyors 132. Another embodiment might use two vats 134 and sixteen conveyors. Further, alternate embodiments may vary the size of the openings 138. FIG. 25 depicts a side view of the exemplary apparatus 126.

The vat 134 contains the whitening compound 118 in liquid form. In order to prevent the compound 118 from hardening inside the vat 134, the vat contents are typically agitated. Such agitation may be constant or intermittent, and may take many forms. For example, the compound 118 may be stirred by a mechanized paddle arrangement, acoustically agitated, or recirculated by a pump and outlet arrangement. That is, liquid whitening compound may continuously flow through an outlet located at or near the vat top, down one or more tubes, and be pumped back into the vat through an inlet port located at or near the vat bottom. The disturbance caused in the liquid by the continuous stream of newly-pumped compound prevents thickening or hardening.

Figure 32:
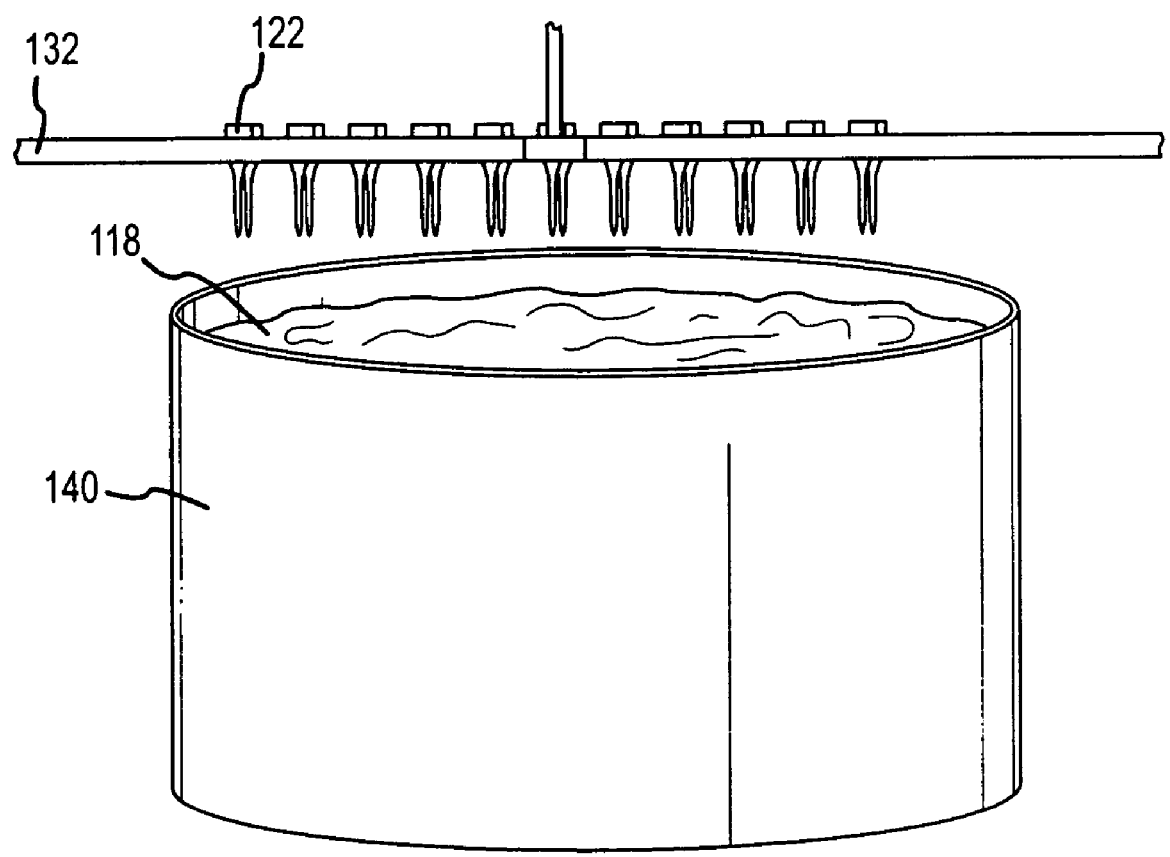
FIG. 32 depicts a row of power dental flossing device tips suspended above a vat of whitening compound.
Figure 33A:
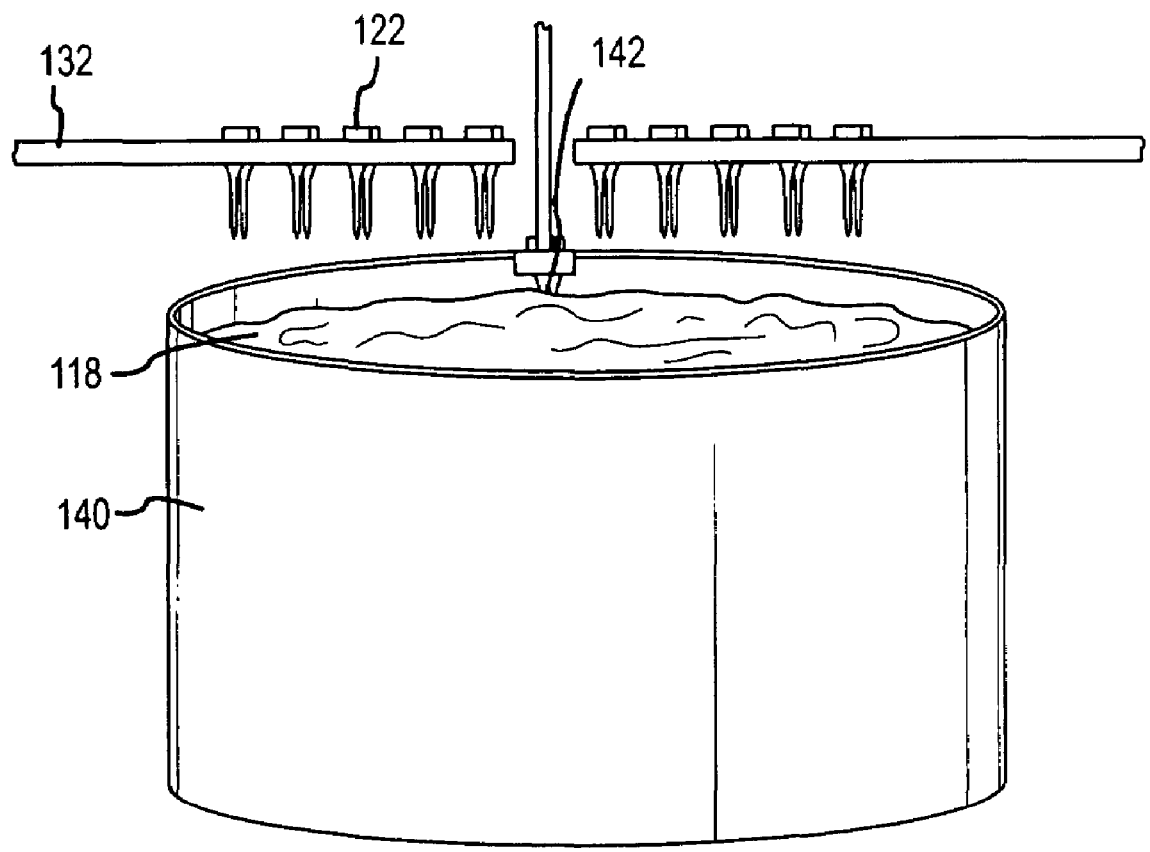
FIG. 33A depicts a single row of power dental flossing device tips inserted in a vat of whitening compound.
Figure 33B:
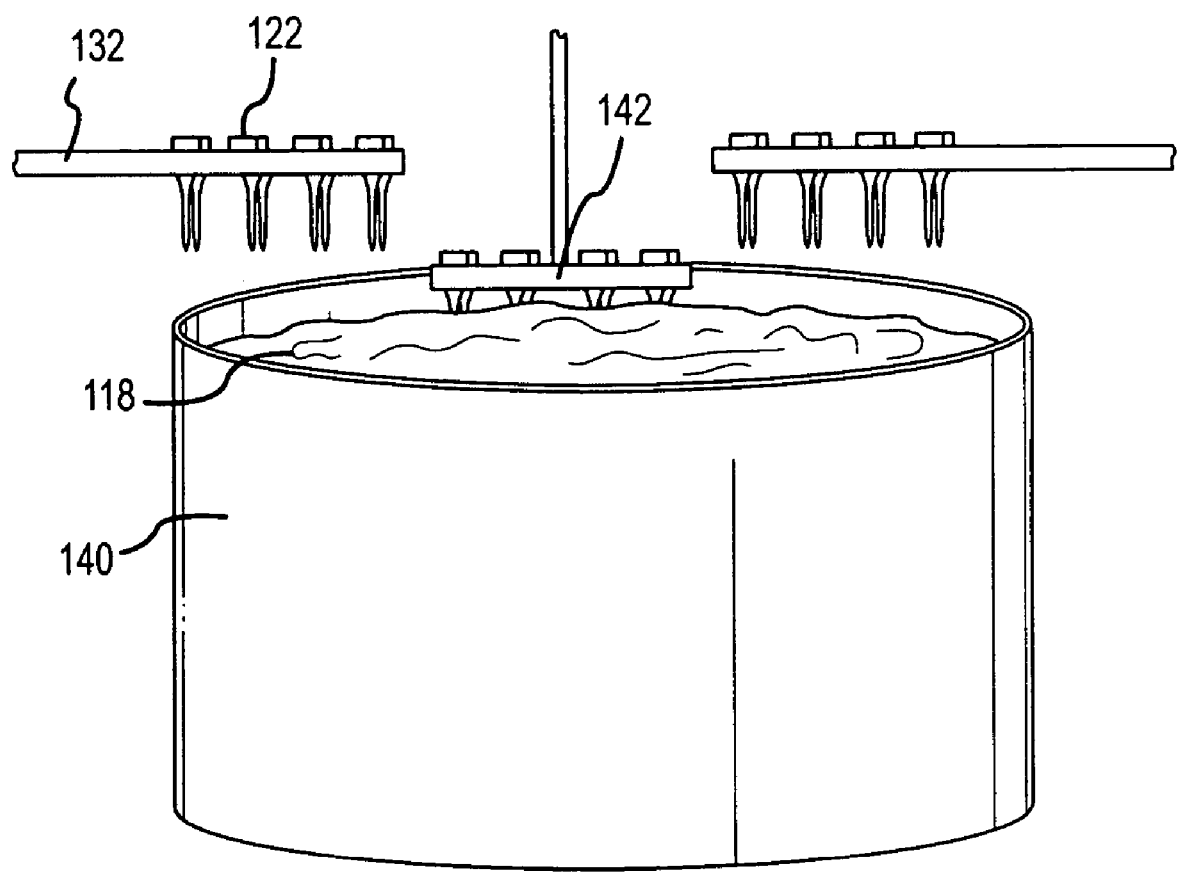
FIG. 33B depicts multiple rows of power dental flossing device tips inserted in a vat of whitening compound.

The conveyors 132 carry the tips 122 into the vat 134 interior through the openings 138, at which point the tips are suspended above the surface of the whitening compound 118, as shown in FIG. 32. The entire vat 134 may be filled with whitening compound 118, or a separate container 140 may be present within the vat to hold the compound, as shown in FIG. 32. The conveyors 132 (or selected portions thereof) are also capable of vertical movement, and may lower the tips 122 into the whitening compound 118. The tips are shown partially inserted in container 140 holding the whitening compound in FIG. 33A. In the present embodiment, tips are dipped into the whitening compound in single rows, although alternate embodiments may dip multiple rows of tips into the whitening compound simultaneously, as shown in FIG. 33B. Tips 122 may be dipped into the whitening compound 118 either by lowering a section 142 of the conveyor or rail 132 upon which tips rest into the container 140, or the tips may be connected to a rotating arm 133. (The top of the arm is shown to best effect in FIGS. 25 and 26.) If a rotating arm is employed, the end of the arm may mate with the tip connection structure, raise the tips, rotate them over the vat or otherwise away from the conveyor, and lower the tips into the vat.

While the tips 122 are suspended in the whitening compound 118, the grafting reaction detailed above bonds the whitening compound to the nylon substrate of each flosser tip. In addition, since the liquid compound is viscous, a portion of it coats and remains on each tip when they are removed from the compound by the rising conveyors.

Figure 26:
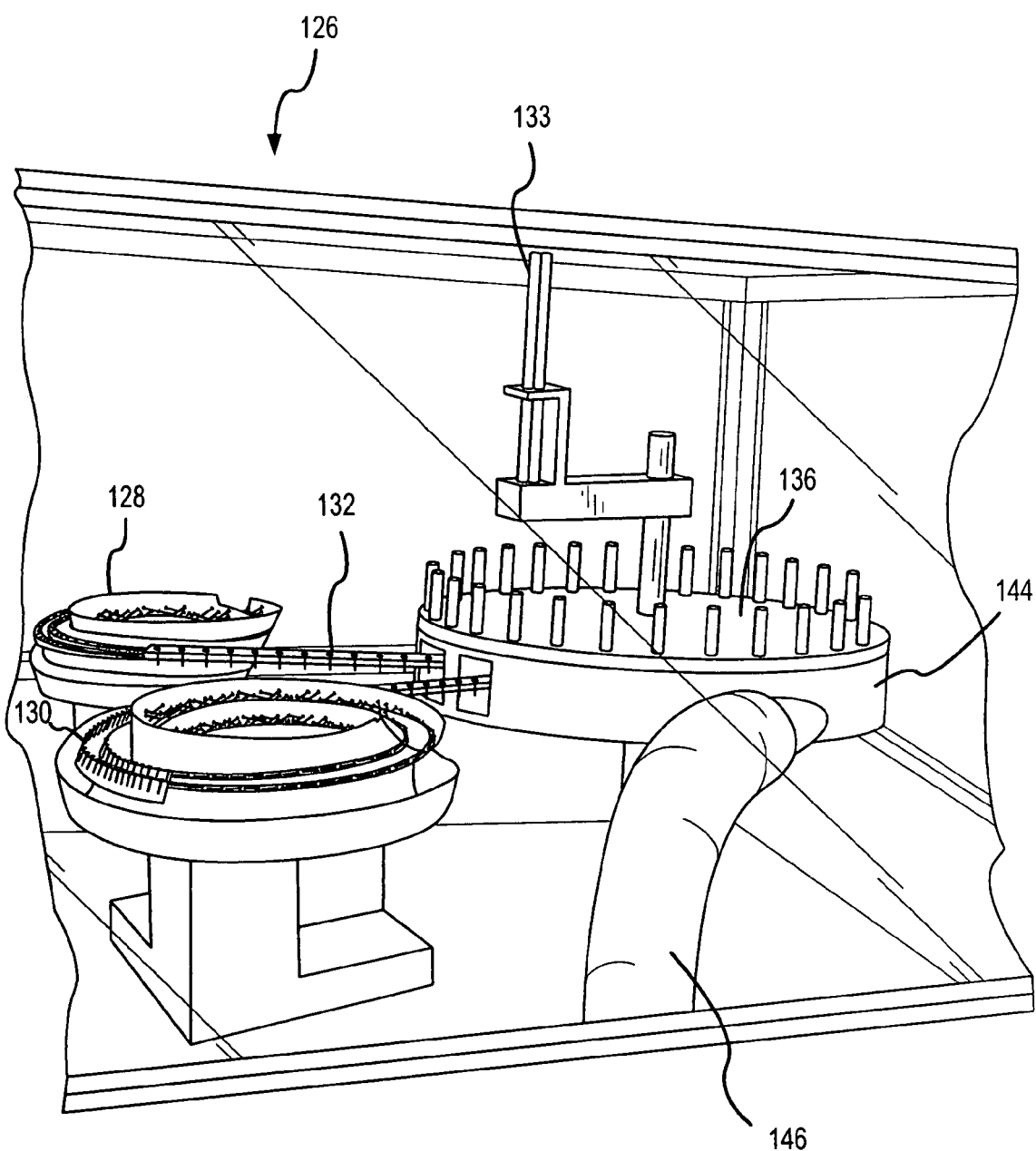
FIG. 26 depicts a side view of an apparatus suitable for coating a power dental flossing device tip with a whitening compound.
Figure 27:
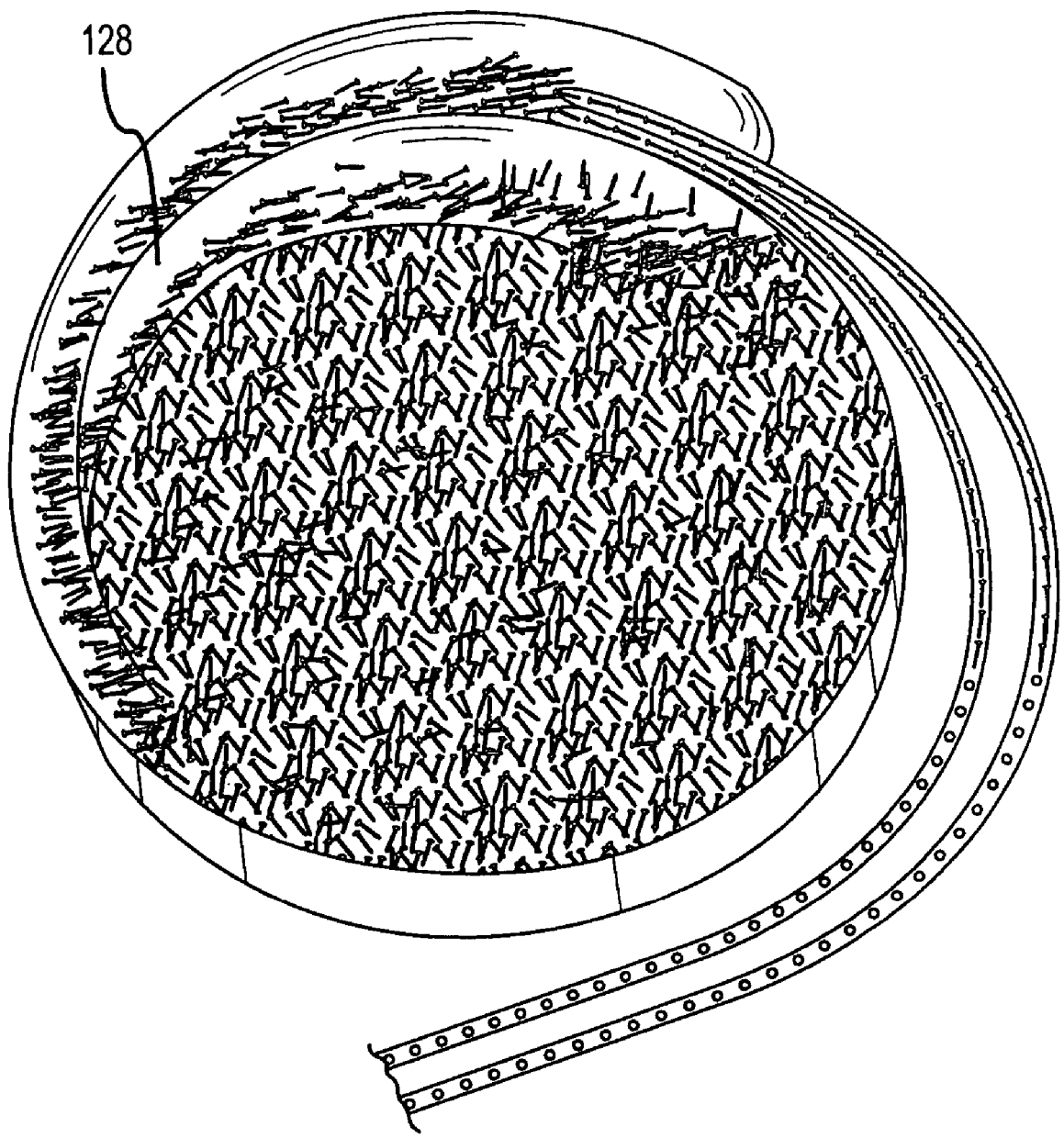
FIG. 27 depicts a top-down view of a hopper containing multiple power dental device flossing tips.
Figure 28:
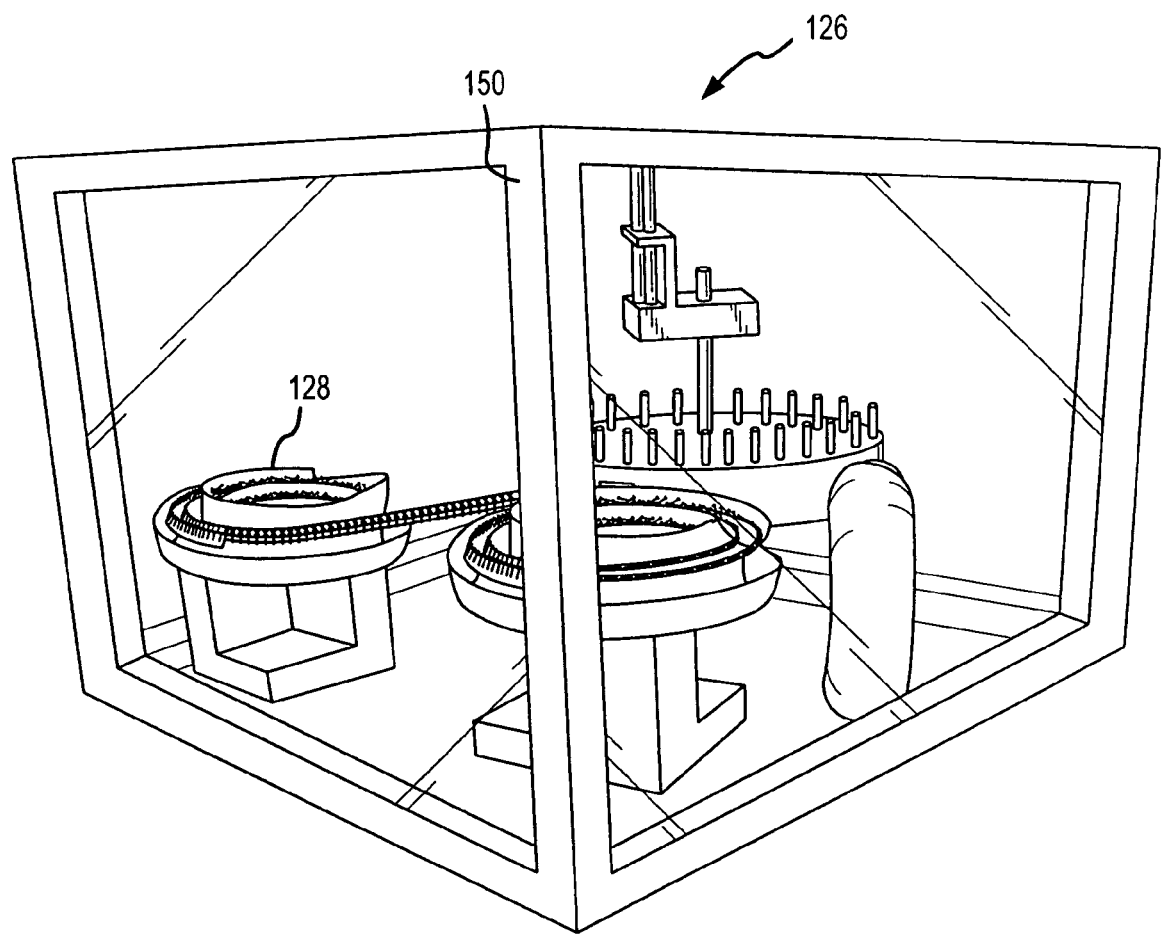
FIG. 28 depicts a fifth view of an apparatus suitable for coating a power dental flossing device tip with a whitening compound.
Figure 29:
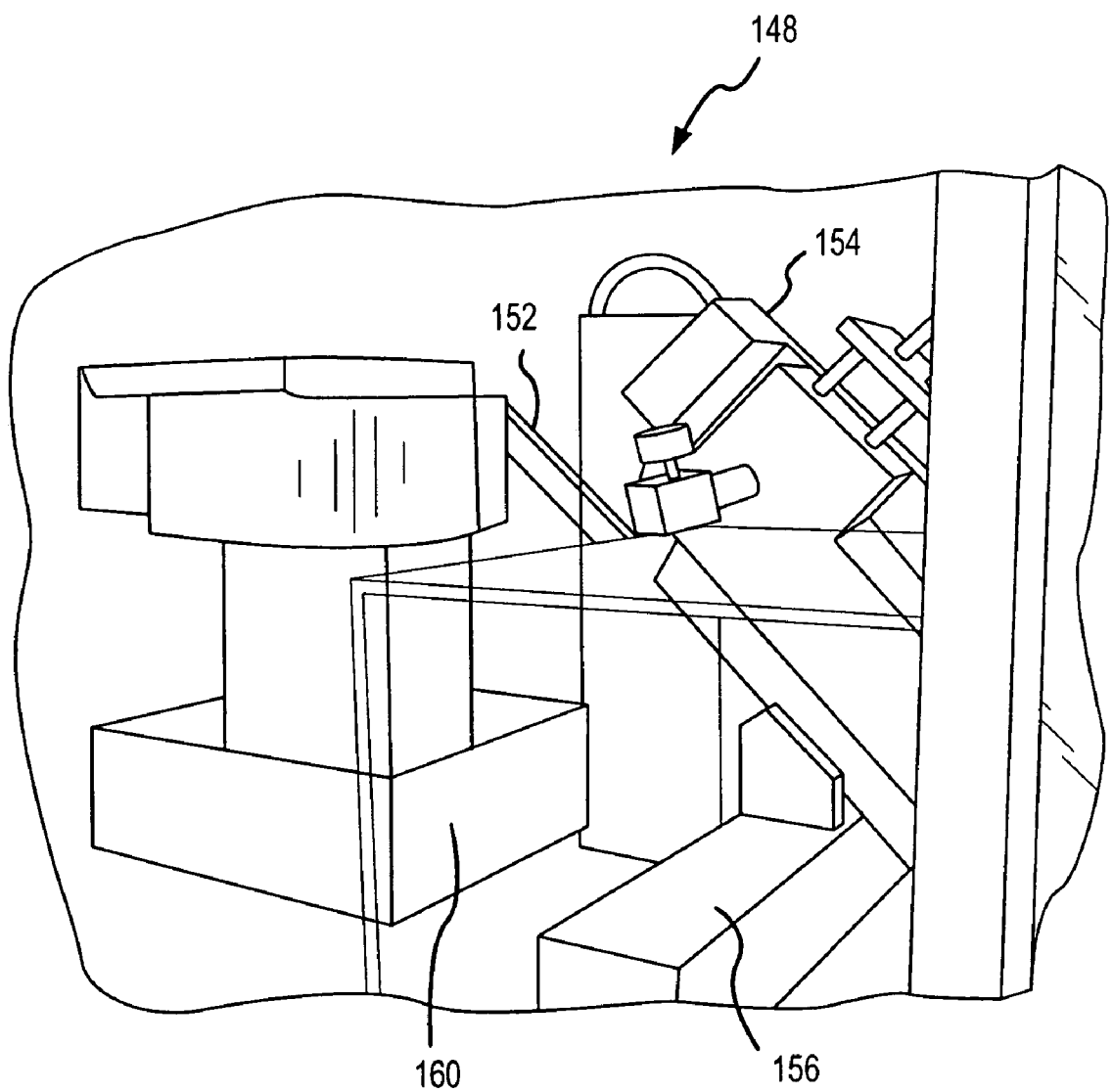
FIG. 29 depicts a first view of a packaging apparatus suitable for packaging a power dental flossing device tip with a whitening compound.

Once coated, the tips 122 are removed from the whitening compound 118, and moved into a drying tunnel 144. The drying tunnel 144 exterior is best shown in FIGS. 25 and 26. In the present embodiment, the tunnel is circular in shape, although alternate embodiments may use differently-shaped drying machines 126. The conveyors move the tip through the drying tunnel in approximately fifteen seconds, at which point the coating dries and hardens on the tips' exteriors. In addition, air may be forced across the tips to speed drying. Heated air may be provided to the drying funnel 144 by a hot air supply tube 146, for example (see FIG. 25). The conveyors 132 finally deposit the tips into a packaging apparatus 148, as shown in FIGS. 27–29. In alternate embodiments, the tips 122 may simply air dry for approximately two to three minutes, rather than being heated. In yet another embodiment, one hopper shown in FIGS. 23 and 24 may be a feed hopper into which tips are placed for conveyance into the vat, while a second hopper may be an exit hopper for collecting coated flosser tips 122.

Additional views of the manufacturing apparatus 126 are depicted in FIGS. 26 through 31. FIG. 26 depicts a side view of the apparatus, showing the feed hoppers 128, drying tunnel 144 exterior, hot air supply hose 146, and related conveyors 130, 132. Also shown is the rotating arm 133 extending through a vat cover 136. The rotating arm 133 facilitates lowering one or more tips into the vat for coating with the whitening compound, as described above with respect to FIGS. 32, 33A, and 33B. Generally, the arm may be pneumatically, hydraulically, or electrically powered, and may move vertically as well as rotationally.

FIG. 27 depicts a top-down view of a feed hopper 128. As shown, the feed hopper typically contains a plurality of uncoated flosser tips. The operation of the feed hopper is described in more detail above, with respect to FIG. 23.

FIG. 28 depicts another view of the manufacturing apparatus 126. The apparatus may be enclosed in a glass, plastic, or metal container 150, as shown. The container generally prevents fumes or chemicals from escaping from the container and into the atmosphere, as well as dust or debris from settling on or in the apparatus 126. The container 150 may also prevent wind or breezes from disturbing or misaligning the tips 122 in the hopper 128 or in the conveyor 132.

Figure 30:
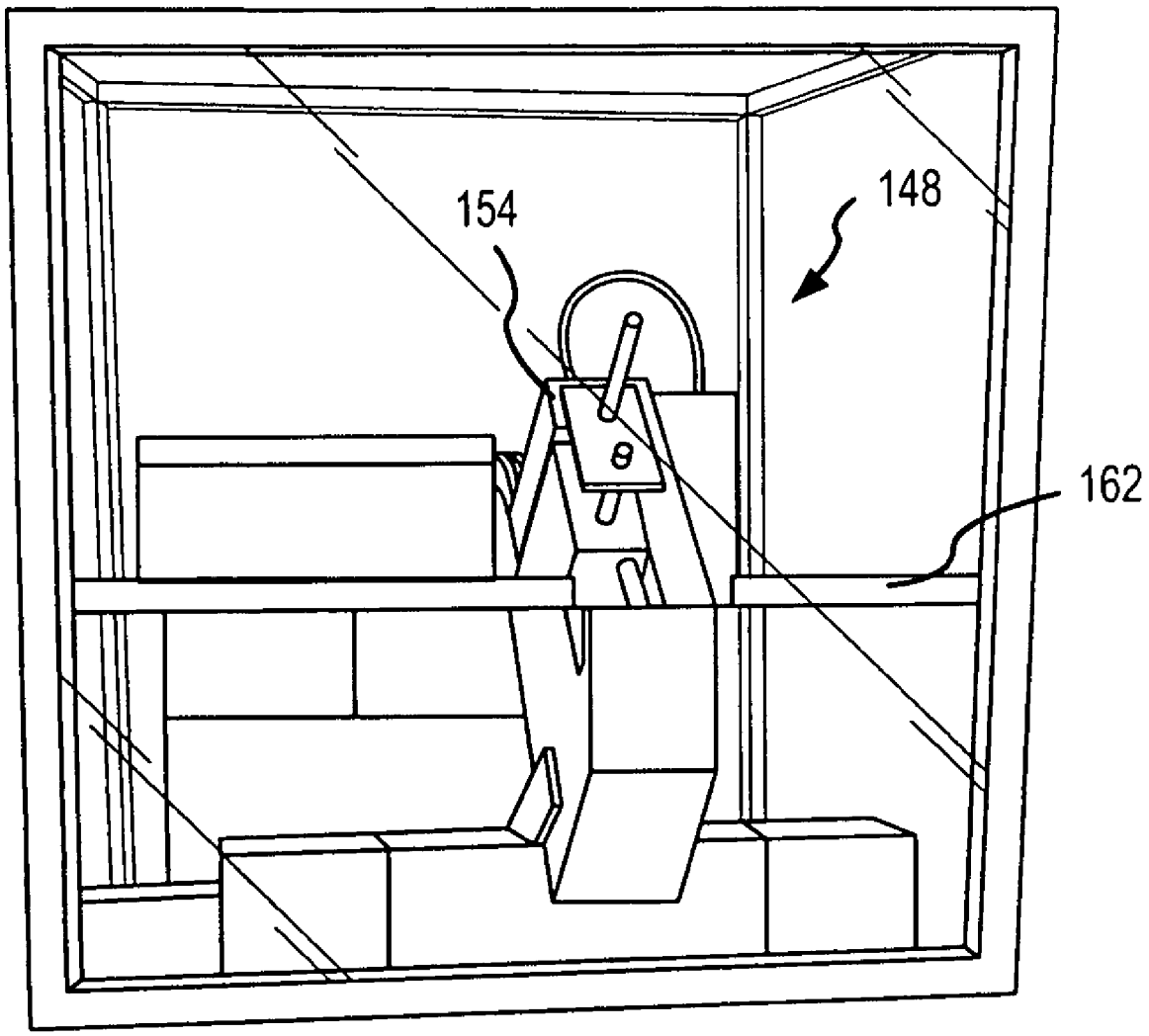
FIG. 30 depicts a second view of a packaging apparatus suitable for packaging a power dental flossing device tip with a whitening compound.
Figure 31:
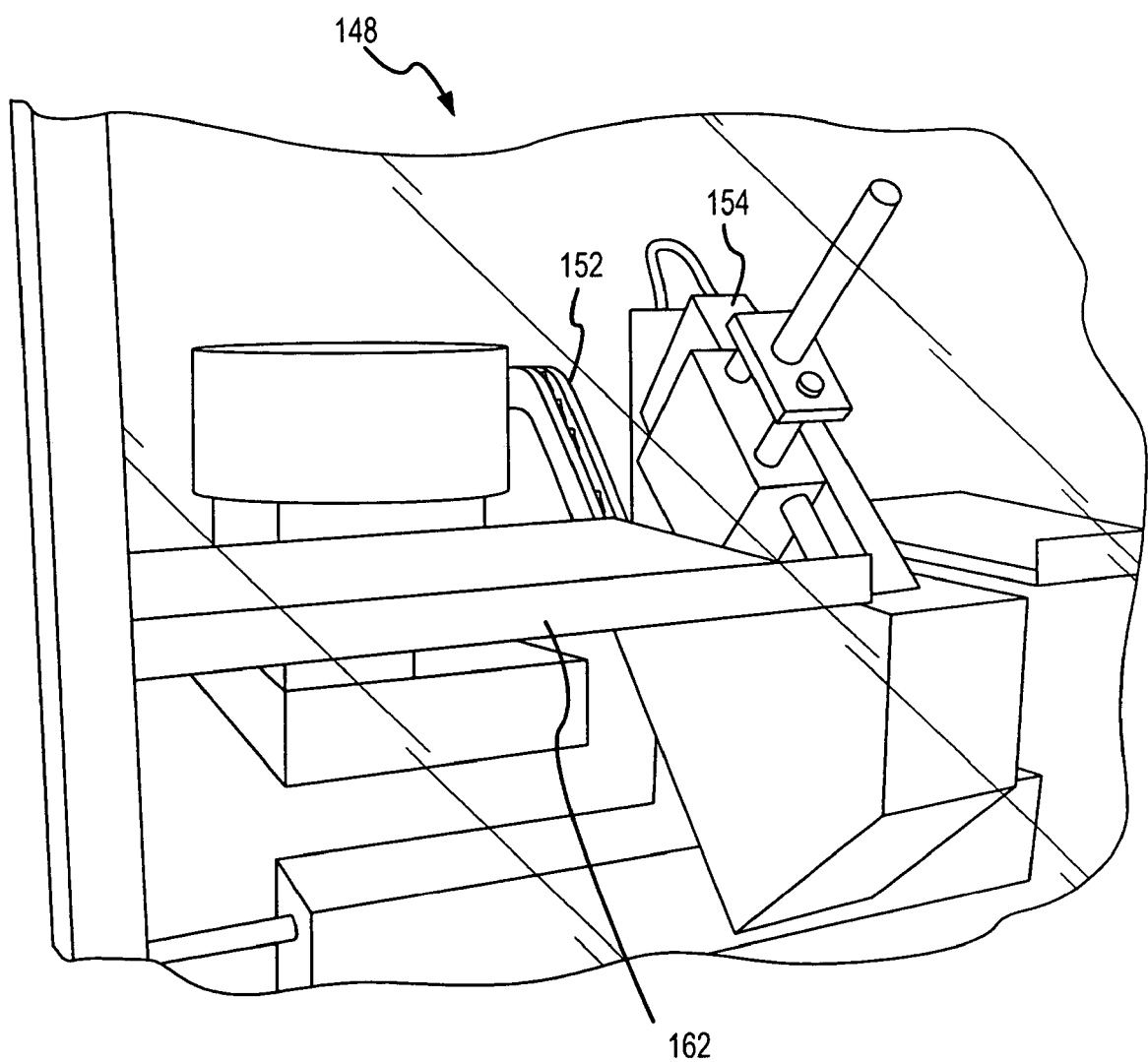
FIG. 31 depicts a third view of a packaging apparatus suitable for packaging a power dental flossing device tip with a whitening compound.

FIGS. 29 through 31 depict the packaging apparatus 148. Some embodiments of the manufacturing apparatus 126 may omit the packaging apparatus 148. Generally, coated power flosser tips 122 exit the vat 134 onto one or more packaging conveyors 152. The packaging conveyors align and move the tips to a packaging arm 154, which places them in tip cartridges 156 as described below.

As the tips 122 move along the packaging conveyors 152, tip cartridges 156 are suspended from a cartridge container 158 and conveyed by a shuttle 160 to the packaging arm 154. The arm presses, or otherwise places, tips 122 into the cartridges. Filled cartridges may be conveyed along the packaging conveyor 152 (or another conveyor to a holding point 162 for collection.)

The packaging arm 154 may move back and forth between adjacent packaging conveyors 152 to place tips on each conveyor into cartridges 156. In some embodiments, the cartridges may have multiple rails or cavities for accepting multiple rows of tips 122. Such cartridges may accept tips 122 from both packaging conveyors 152.

In an alternate embodiment, the whitening compound may be sprayed onto the flosser tips. A sprayer may coat the tips with the compound as the tips move along the conveyor, rather than having the tips dip into a vat containing the compound. In yet another embodiment, the sprayer may be mobile while the tips remain relatively stationary. In such an embodiment, the sprayer may (for example) be affixed to a robotic arm, conveyor, or slide back and forth on rails, facilitating the deposit of whitening compound across multiple tips spaced, for example, along a rack. The sprayer may further rotate or otherwise move around one or more flosser tips, permitting a single sprayer to deposit whitening compound across substantially all surfaces of a flosser tip.

In yet another embodiment, both sprayer and tips may be mobile, permitting the sprayer and tips to move independently of one another. Such an embodiment may shorten the time required to deposit the whitening compound on one or more tips.

Generally, the foregoing embodiments have described multiple methods by which a whitening compound may be coated or otherwise added to a flosser tip after the tip is molded or formed, for example from a plastic. In yet another embodiment, the material used to form a flosser tip may include the above-described whitening compound as an integral portion thereof. In such an embodiment, the whitening compound may not be added to the exterior of the tip, as previously described. Instead, the whitening compound may be molded into or s part of the material forming the tip. Thus, once the tip is formed, the whitening compound is present as part of the tip, and need not be applied separately. In yet other embodiments, additional whitening compound may be added, in any of the manners described herein, to the exterior of a tip formed from a material incorporating a whitening compound.

In a further embodiment, a flosser tip may be encased in a mold, into which a whitening compound may be injected. In this manner, the whitening compound may surround the tip, occupying a cavity or space between the tip exterior and interior sidewall of the mold. The exact contours and shape of the whitening compound may thus be carefully controlled, so that specific shapes and configurations may be created as desired. For example, a flosser tip having a point elongated along a lateral axis of the tip may be created, in order to define a narrow, toothpick-like shape facilitating insertion of the whitening compound between adjacent teeth or between a tooth and gum.

The manufacturing apparatus may be enclosed in order to minimize particles settling on the tips. Although this may not be necessary, it may facilitate keeping the vat, tips, conveyor, and other items free from dust, grit, particulates, and so forth.

While the invention has been particularly shown and described with reference to specific embodiments thereof, it will be understood by those skilled in the art that various other changes in the form and details may be made without departing from the spirit and scope of the invention. For example, the whitening compound's chemical formulae may be altered, the tips may be air-dried instead of heat-dried, a different chemical whitening agent may be employed, and so forth. Further, additional material or chemicals may be added to the whitening compound, such as fruit flavoring agents or breath fresheners. Accordingly, the proper scope of the invention is defined by the appended claims.

The invention claimed is:

1. A tip for a power dental flossing device, comprising:
 a base portion for supporting the tip when coupled to the dental flossing device;
 a central portion having a substantially rectangular cross-section, and having a first end and a second end, said first end coupled to said base portion, wherein said central portion has a height and a width;
 an end portion coupled to said second end of said central portion, for insertion between a pair of adjacent teeth of a user, wherein said end portion has a height and a width; and
 a whitening compound substantially enclosing said end portion and bonded to said end portion by a monomer.

2. The tip of claim 1, wherein the whitening compound contains abrasive particles.

3. The tip of claim 2, wherein the whitening compound reacts with saliva.

4. The tip of claim 3, wherein the whitening compound dissolves upon contact with saliva.

5. The tip of claim 3, wherein the whitening compound foams upon contact with saliva.

6. The tip of claim 1, wherein the whitening compound comprises:
 a flavoring agent; and
 an abrasive particulate.

7. The tip of claim 1, wherein the whitening compound comprises:
 a whitening agent; and
 a polymer; wherein
 the whitening agent is chemically bonded to the polymer; and
 the polymer is chemically bonded to the tip.

8. The tip of claim 7, wherein the whitening agent is a chemical whitening agent.

9. The tip of claim 7, wherein the whitening agent is an abrasive whitening agent.

10. A whitening flosser tip, comprising:
 a flosser tip; and
 a whitening compound bonded to the flosser tip by a monomer, the whitening compound comprising:
  a drying retardant agent;
  an acrylic prepolymer;
  a wetting agent; and
  an abrasive agent.

11. The whitening flosser tip of claim 10, wherein the whitening compound further comprises:
 a flavoring;
 calcium carbonate;
 a white filler; and
 a thickener.

12. The whitening flosser tip of claim 11, wherein the abrasive is sylodent 700.

13. The whitening flosser tip of claim 11, wherein the whitening compound further comprises a chemical whitener.

14. The whitening flosser tip of claim 13, wherein the whitening compound further comprises an anti-microbial solution.

* * * * *